US011738195B2

(12) United States Patent
Young et al.

(10) Patent No.: US 11,738,195 B2
(45) Date of Patent: Aug. 29, 2023

(54) ELECTRICAL STIMULATION DEVICE FOR APPLYING FREQUENCY AND PEAK VOLTAGE HAVING INVERSE RELATIONSHIP

(71) Applicant: NuEnerchi, Inc., San Mateo, CA (US)

(72) Inventors: Sam Ira Young, San Jose, CA (US); Jeffrey Karl Lucas, San Carlos, CA (US); Bruce Wayne Nash, East Palo Alto, CA (US); John R Haggis, San Jose, CA (US); Robert M Salter, III, Saratoga, CA (US)

(73) Assignee: NuEnerchi, Inc., San Mateo, CA (US)

( * ) Notice: Subject to any disclaimer, the term of this patent is extended or adjusted under 35 U.S.C. 154(b) by 191 days.

(21) Appl. No.: 16/673,615

(22) Filed: Nov. 4, 2019

(65) Prior Publication Data

US 2020/0171305 A1 Jun. 4, 2020

Related U.S. Application Data

(60) Provisional application No. 62/769,997, filed on Nov. 20, 2018.

(51) Int. Cl.
*A61N 1/36* (2006.01)
*A61H 99/00* (2006.01)
*A61N 1/04* (2006.01)

(52) U.S. Cl.
CPC ......... *A61N 1/36034* (2017.08); *A61H 99/00* (2013.01); *A61N 1/0476* (2013.01); *A61N 1/36031* (2017.08); *A61H 2201/10* (2013.01)

(58) Field of Classification Search
CPC .............. A61N 1/0456; A61N 1/36014; A61N 1/36034; A61N 1/18
See application file for complete search history.

(56) References Cited

U.S. PATENT DOCUMENTS 3,785,383 A    1/1974 Dotto
3,902,502 A    9/1975 Liss et al.
(Continued)

FOREIGN PATENT DOCUMENTS

CN    107441620    12/2017
CN    207722235    8/2018
(Continued)

OTHER PUBLICATIONS

International Search Report and Written Opinion received in PCT/US2019/059492 dated Feb. 6, 2020.
(Continued)

*Primary Examiner* — Michael J D'Abreu
(74) *Attorney, Agent, or Firm* — Knobbe, Martens, Olson & Bear, LLP

(57) ABSTRACT

A portable electrical stimulation device is disclosed. In one aspect, the device includes a pair of electrodes configured to be electrically coupled to a user and a wave generator configured to provide an electrical signal to the user via the pair of electrodes. The wave generator is further configured to generate the electrical signal at one of a plurality of levels. Each of the plurality of levels is defined by at least a frequency, a peak voltage, and a peak current. For each of the levels the frequency is in a range of about 50 Hz-about 500 Hz, the peak voltage is in a range of about 40 V-about 250 V, the peak current is in a range of about 25 mA-about 150 mA, and the frequency and the peak voltage have a generally inverse relationship.

21 Claims, 16 Drawing Sheets

(56) References Cited

U.S. PATENT DOCUMENTS

| | | |
|---|---|---|
| 4,019,510 A | 4/1977 | Ellis |
| 4,112,923 A | 9/1978 | Tomecek |
| 4,177,819 A | 12/1979 | Kofsky et al. |
| 4,232,678 A | 11/1980 | Skovajsa |
| 4,232,680 A | 11/1980 | Hudleson et al. |
| 4,338,945 A | 7/1982 | Kosugi et al. |
| 4,535,777 A | 8/1985 | Castel |
| 4,535,784 A | 8/1985 | Rohlicek et al. |
| 4,553,546 A | 11/1985 | Javelle |
| 4,646,743 A | 3/1987 | Parris |
| 4,719,922 A | 1/1988 | Padjen et al. |
| 4,844,075 A | 7/1989 | Liss et al. |
| 4,856,526 A | 8/1989 | Liss et al. |
| 4,989,605 A | 2/1991 | Rossen |
| 5,109,847 A | 5/1992 | Liss et al. |
| 5,195,517 A | 3/1993 | Chen |
| 5,304,207 A | 4/1994 | Stromer |
| 5,397,338 A | 3/1995 | Grey et al. |
| 5,441,528 A | 8/1995 | Chang et al. |
| 5,464,436 A | 11/1995 | Smith |
| 5,476,481 A | 12/1995 | Schondorf |
| 5,487,759 A | 1/1996 | Bastyr et al. |
| 5,501,704 A | 3/1996 | Chang et al. |
| 5,514,175 A | 5/1996 | Kim et al. |
| 5,540,735 A | 7/1996 | Wingrove |
| 5,634,939 A | 6/1997 | Kuster et al. |
| 5,776,170 A | 7/1998 | MacDonald et al. |
| 5,782,894 A | 7/1998 | Israel |
| 5,797,854 A | 8/1998 | Hedgecock |
| 5,861,015 A | 1/1999 | Benja-Athon |
| 5,861,017 A | 1/1999 | Smith et al. |
| 5,871,506 A | 2/1999 | Mower |
| 6,035,236 A | 3/2000 | Jarding et al. |
| 6,136,019 A | 10/2000 | Mower |
| 6,141,587 A | 10/2000 | Mower |
| 6,248,056 B1 | 6/2001 | Persson |
| 6,275,735 B1 | 8/2001 | Jarding et al. |
| 6,332,096 B1 | 12/2001 | Mower |
| 6,337,995 B1 | 1/2002 | Mower |
| 6,341,235 B1 | 1/2002 | Mower |
| 6,343,232 B1 | 1/2002 | Mower |
| 6,393,328 B1 | 5/2002 | McGraw et al. |
| 6,411,845 B1 | 6/2002 | Mower |
| 6,411,847 B1 | 6/2002 | Mower |
| 6,445,955 B1 | 9/2002 | Michelson et al. |
| 6,560,487 B1 | 5/2003 | McGraw et al. |
| 6,564,103 B2 | 5/2003 | Fischer et al. |
| 6,567,702 B1 | 5/2003 | Nekhendzy et al. |
| 6,584,358 B2 | 6/2003 | Carter et al. |
| 6,671,557 B1 | 12/2003 | Gliner |
| 6,675,048 B2 | 1/2004 | McGraw et al. |
| 6,697,670 B2 | 2/2004 | Chomenky et al. |
| 6,704,603 B1 | 3/2004 | Gesotti |
| 6,760,627 B2 | 7/2004 | Carter et al. |
| 6,778,854 B2 | 8/2004 | Puskas |
| 6,788,976 B2 | 9/2004 | Gesotti |
| 6,792,315 B2 | 9/2004 | Carter et al. |
| 6,853,863 B2 | 2/2005 | Carter et al. |
| 6,879,859 B1 | 4/2005 | Boveja |
| 6,895,274 B2 | 5/2005 | Mower |
| 6,988,005 B2 | 1/2006 | McGraw et al. |
| 7,013,179 B2 | 3/2006 | Carter et al. |
| 7,130,696 B2 | 10/2006 | Carter et al. |
| 7,158,834 B2 | 1/2007 | Paul, Jr. |
| 7,187,977 B2 | 3/2007 | Paul, Jr. |
| 7,198,633 B1 | 4/2007 | Starwynn |
| 7,203,537 B2 | 4/2007 | Mower |
| 7,228,184 B2 | 6/2007 | Heath |
| 7,310,552 B2 | 12/2007 | Puskas |
| 7,340,299 B2 | 3/2008 | Puskas |
| 7,343,203 B2 | 3/2008 | Reinhold |
| RE40,279 E | 4/2008 | Sluijter et al. |
| 7,369,896 B2 | 5/2008 | Gesotti |
| 7,386,349 B2 | 6/2008 | Davar |
| 7,440,800 B2 | 10/2008 | Mower |
| 7,503,927 B1 | 3/2009 | Vetanze |
| 7,509,165 B2 | 3/2009 | Smith et al. |
| 7,591,849 B2 | 9/2009 | Richardson |
| 7,613,517 B2 | 11/2009 | Goroszeniuk |
| RE41,045 E | 12/2009 | Sluijter et al. |
| 7,643,876 B2 | 1/2010 | Zhang et al. |
| 7,662,179 B2 | 2/2010 | Sarfarazi |
| 7,715,910 B2 | 5/2010 | Hargrove et al. |
| 7,747,332 B2 | 6/2010 | McGraw et al. |
| 7,826,900 B2 | 11/2010 | Stellar et al. |
| 7,840,264 B1 | 11/2010 | Mower |
| 7,873,421 B2 | 1/2011 | Karell |
| 7,904,150 B2 | 3/2011 | Smith et al. |
| 7,908,003 B1 | 3/2011 | Mower |
| 7,912,541 B2 | 3/2011 | Smith et al. |
| 7,979,121 B2 | 7/2011 | Azure |
| 7,979,137 B2 | 7/2011 | Tracey et al. |
| 7,981,062 B2 | 7/2011 | Chow et al. |
| 8,121,696 B2 | 2/2012 | Vallero |
| 8,126,530 B2 | 2/2012 | Bare et al. |
| 8,160,696 B2 | 4/2012 | Bendett et al. |
| 8,165,695 B2 | 4/2012 | DiUbaldi et al. |
| 8,170,683 B2 | 5/2012 | Wahlgren et al. |
| 8,185,207 B2 | 5/2012 | Molnar et al. |
| 8,260,439 B2 | 9/2012 | DiUbaldi et al. |
| 8,280,502 B2 | 10/2012 | Hargrove et al. |
| 8,290,585 B2 | 10/2012 | Mower |
| 8,317,848 B1 | 11/2012 | Webb et al. |
| 8,340,756 B2 | 12/2012 | Picciano |
| 8,352,026 B2 | 1/2013 | DiUbaldi |
| 8,357,187 B1 | 1/2013 | Bendett et al. |
| 8,428,735 B2 | 4/2013 | Littlewood et al. |
| 8,447,399 B2 | 5/2013 | Mower |
| 8,463,389 B2 | 6/2013 | Oths |
| 8,475,506 B1 | 7/2013 | Bendett et al. |
| 8,483,832 B2 | 7/2013 | Simon |
| 8,498,699 B2 | 7/2013 | Wells et al. |
| 8,506,613 B2 | 8/2013 | Webb et al. |
| 8,551,150 B1 | 10/2013 | Webb et al. |
| 8,556,967 B2 | 10/2013 | Sarfarazi |
| 8,560,075 B2 | 10/2013 | Covalin |
| 8,565,885 B2 | 10/2013 | Chen et al. |
| 8,583,256 B2 | 11/2013 | Tracey et al. |
| 8,588,930 B2 | 11/2013 | DiUbaldi et al. |
| 8,613,766 B2 | 12/2013 | Richardson et al. |
| 8,620,438 B1 | 12/2013 | Wijting et al. |
| 8,632,577 B1 | 1/2014 | Bendett et al. |
| 8,644,942 B1 | 2/2014 | Diemer |
| 8,652,187 B2 | 2/2014 | Wells et al. |
| 8,653,352 B2 | 2/2014 | Wauke |
| 8,709,078 B1 | 4/2014 | Friend et al. |
| 8,731,657 B1 | 5/2014 | Shambayati et al. |
| 8,744,570 B2 | 6/2014 | Lee et al. |
| 8,747,447 B2 | 6/2014 | Stafford et al. |
| 8,751,003 B2 | 6/2014 | DiUbaldi et al. |
| 8,755,892 B2 | 6/2014 | Amurthur et al. |
| 8,755,903 B2 | 6/2014 | Hou et al. |
| 8,761,874 B2 | 6/2014 | Mantle et al. |
| 8,768,472 B2 | 7/2014 | Fang et al. |
| 8,774,926 B2 | 7/2014 | Alataris et al. |
| 8,788,044 B2 | 7/2014 | John |
| 8,792,978 B2 | 7/2014 | Wells et al. |
| 8,834,545 B2 | 9/2014 | Stafford et al. |
| 8,840,654 B2 | 9/2014 | Stafford et al. |
| 8,864,806 B2 | 10/2014 | Wells et al. |
| 8,874,205 B2 | 10/2014 | Simon et al. |
| 8,894,697 B2 | 11/2014 | Stafford et al. |
| 8,929,973 B1 | 1/2015 | Webb et al. |
| 8,945,197 B1 | 2/2015 | Friend et al. |
| 8,956,396 B1 | 2/2015 | Friend et al. |
| 8,968,376 B2 | 3/2015 | Wells et al. |
| 8,972,016 B2 | 3/2015 | Thomas et al. |
| 8,983,596 B2 | 3/2015 | Mantle et al. |
| 8,983,621 B2 | 3/2015 | Hou et al. |
| 8,985,119 B1 | 3/2015 | Webb et al. |
| 8,996,131 B1 | 3/2015 | Owen et al. |
| 8,998,914 B2 | 4/2015 | Stafford et al. |
| 9,037,248 B2 | 5/2015 | Durand et al. |
| 9,037,269 B2 | 5/2015 | Schroeder |

(56) References Cited

U.S. PATENT DOCUMENTS

| | | |
|---|---|---|
| 9,067,054 B2 | 6/2015 | Simon et al. |
| 9,168,374 B2 | 10/2015 | Su |
| 9,186,506 B2 | 11/2015 | Johnson |
| 9,242,092 B2 | 1/2016 | Simon et al. |
| 9,302,117 B2 | 4/2016 | De Vincentiis |
| 9,308,363 B2 | 4/2016 | Goroszeniuk et al. |
| 9,333,347 B2 | 5/2016 | Simon et al. |
| 9,339,642 B1 | 5/2016 | Bikson et al. |
| 9,421,123 B2 | 8/2016 | Lee et al. |
| 9,421,358 B2 | 8/2016 | Skaribas et al. |
| 9,440,077 B2 | 9/2016 | Popovic et al. |
| 9,656,070 B2 | 5/2017 | Gozani et al. |
| 9,662,269 B2 | 5/2017 | Brown et al. |
| 9,717,904 B2 | 8/2017 | Simon et al. |
| 9,764,133 B2 | 9/2017 | Thomas et al. |
| 9,855,426 B2 | 1/2018 | Cakmak et al. |
| 9,878,154 B2 | 1/2018 | Tai |
| 9,889,296 B2 | 2/2018 | Zhu |
| 9,925,375 B2 | 3/2018 | Esh et al. |
| 9,974,947 B2 | 5/2018 | Durand et al. |
| 9,993,647 B2 | 6/2018 | Li et al. |
| 2002/0068961 A1 | 6/2002 | Fischer et al. |
| 2003/0149451 A1 | 8/2003 | Chomenky et al. |
| 2007/0225769 A1 | 9/2007 | Smith et al. |
| 2009/0112284 A1 | 4/2009 | Smith et al. |
| 2009/0287264 A1 | 11/2009 | Paret |
| 2009/0287284 A1 | 11/2009 | Soong et al. |
| 2010/0004715 A1* | 1/2010 | Fahey .................. A61N 1/0476 607/48 |
| 2011/0208257 A1 | 8/2011 | Labuschagne |
| 2012/0265048 A1 | 10/2012 | Biggs et al. |
| 2012/0303077 A1 | 11/2012 | De Vincentiis |
| 2013/0061736 A1 | 3/2013 | Wauke |
| 2013/0085420 A1 | 4/2013 | Feinstein |
| 2013/0138178 A1 | 5/2013 | Lin et al. |
| 2014/0257448 A1 | 9/2014 | Arle et al. |
| 2015/0005840 A1 | 1/2015 | Pal et al. |
| 2015/0112404 A1 | 4/2015 | Holding et al. |
| 2015/0321000 A1 | 11/2015 | Rosenbluth et al. |
| 2015/0328450 A1 | 11/2015 | Afargan et al. |
| 2015/0335887 A1 | 11/2015 | Riddle et al. |
| 2016/0250465 A1 | 9/2016 | Simon et al. |
| 2017/0020598 A1 | 1/2017 | Millis et al. |
| 2017/0056643 A1 | 3/2017 | Herb et al. |
| 2017/0095667 A1 | 4/2017 | Yakovlev et al. |
| 2018/0036531 A1 | 2/2018 | Schwarz et al. |
| 2018/0085586 A1 | 3/2018 | Stanslaski et al. |
| 2018/0117322 A1 | 5/2018 | Chang et al. |
| 2018/0133472 A1 | 5/2018 | Tai |
| 2018/0133482 A1 | 5/2018 | Zou et al. |
| 2018/0178015 A1 | 6/2018 | Dearden et al. |
| 2018/0214692 A1 | 8/2018 | Esh et al. |
| 2018/0229038 A1 | 8/2018 | Burdick et al. |
| 2018/0250511 A1 | 9/2018 | Black et al. |
| 2018/0264265 A1 | 9/2018 | Black et al. |

FOREIGN PATENT DOCUMENTS

| | | | |
|---|---|---|---|
| CN | 209713992 | 12/2019 | |
| DE | 10141649 B4 | 5/2008 | |
| EP | 0058105 A2 | 8/1982 | |
| EP | 0965358 A2 * | 12/1999 | ............ A61N 1/0492 |
| EP | 1009478 A1 | 6/2000 | |
| EP | 1096970 A1 | 5/2001 | |
| EP | 1294443 A1 | 3/2003 | |
| EP | 1967226 A1 | 9/2008 | |
| EP | 1985332 A1 | 10/2008 | |
| EP | 2550992 A1 | 1/2013 | |
| FR | 2371935 A1 | 6/1978 | |
| FR | 2738155 A1 * | 3/1997 | ............ A61N 1/322 |
| JP | H07116267 A | 5/1995 | |
| JP | 09-047516 A | 2/1997 | |
| JP | 2000-116797 A | 4/2000 | |
| JP | 3193996 U | 10/2014 | |
| JP | 2018-050879 A | 4/2018 | |
| TW | M546814 | 8/2017 | |
| TW | 1619524 | 4/2018 | |
| TW | 201838680 | 11/2018 | |
| TW | M570161 | 11/2018 | |
| WO | WO 1994022529 A1 | 10/1994 | |
| WO | WO 1994028966 A1 | 12/1994 | |
| WO | WO 1998025667 A1 | 6/1998 | |
| WO | WO 1998040121 A1 | 9/1998 | |
| WO | WO 2000002622 A1 | 1/2000 | |
| WO | WO 2003105945 A2 | 12/2003 | |
| WO | WO 2003105955 A1 | 12/2003 | |
| WO | WO 2005/046787 | 5/2005 | |
| WO | WO 2005061049 A1 | 7/2005 | |
| WO | WO 2006000015 A1 | 1/2006 | |
| WO | WO 2006062728 A1 | 6/2006 | |
| WO | WO 2006101917 A2 | 9/2006 | |
| WO | WO 2010032111 A2 | 3/2010 | |
| WO | WO 2010102179 A1 | 9/2010 | |
| WO | WO 2013/106644 | 7/2013 | |
| WO | WO 2018/064991 | 4/2018 | |
| WO | WO 2018/129280 | 7/2018 | |

OTHER PUBLICATIONS

Examination Report received in Indian Patent Application No. 202117027078 dated Mar. 7, 2022.

Office Action received in Application JP 2021-526416, dated Jun. 21, 2022.

* cited by examiner

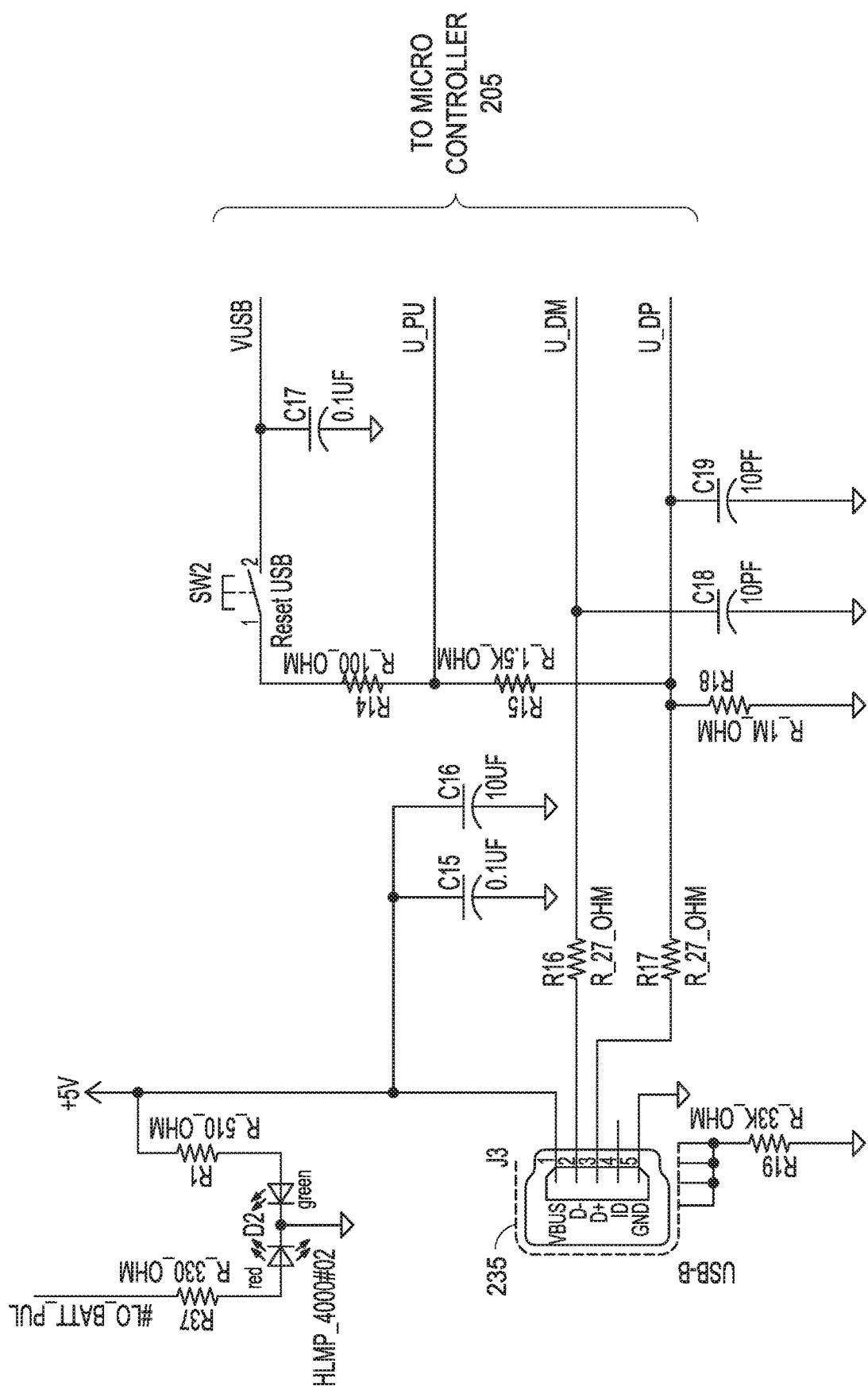

ELECTRICAL STIMULATION DEVICE FOR APPLYING FREQUENCY AND PEAK VOLTAGE HAVING INVERSE RELATIONSHIP

RELATED APPLICATIONS

This application claims priority to and the benefit of Provisional Application No. 62/769,997 filed on Nov. 20, 2018 in the U.S. Patent and Trademark Office, the entire contents of which are incorporated herein by reference.

BACKGROUND

Technological Field

The described technology generally relates to an electrical stimulation device, and in particular, to a unique electrotherapy technology for preventive care, injury recovery, pain management and overall wellness for the sports, fitness, health and/or wellness industries.

Description of the Related Technology

Portable electrical stimulation devices can be used to provide relief to inflamed, sore muscles, joints, and related tissues. One example of such a device is a transcutaneous electrical nerve stimulation (TENS) device. Portable electrical stimulation devices may generate a low voltage electric current which can be applied to a user in order to treat certain conditions, such as inflamed, sore muscles, joints, and related tissues. Many commercially available TENS devices are generally ineffective in that they provide at best temporary pain relief and frequently cause some discomfort to patients and users while they are being treated.

SUMMARY

One inventive aspect is a portable electrical stimulation device, comprising: a pair of electrodes configured to be electrically coupled to a user; and a wave generator configured to provide an electrical signal to the user via the pair of electrodes, wherein the wave generator is further configured to generate the electrical signal at one of a plurality of levels, each of the plurality of levels defined by at least a frequency, a peak voltage, and a peak current, and wherein for each of the levels: the frequency is in a range of about 50 Hz-about 500 Hz, the peak voltage is in a range of about 40 V-about 250 V, the peak current is in a range of about 25 mA-about 150 mA, and the frequency and the peak voltage have a generally inverse relationship.

In certain embodiments, the wave generator is further configured to generate waves that have a strictly positive voltage.

In certain embodiments, the wave generator is further configured to: generate waves having a substantially equal positive pulse width, and adjust the frequency of each of the levels by altering a neutral pulse width of the waves.

In certain embodiments, the wave generator is further configured to: receive a command to transition from a first level to a second level that is different from the first level, gradually increase the peak voltage of waves to the peak voltage associated with the second level in response to the received command.

In certain embodiments, the wave generator comprises a current limiter arranged in series with an output of the wave generator.

In certain embodiments, the current limiter comprises a resistive element and/or or a negative temperature coefficient (NTC) thermistor.

Another aspect is a portable electrical stimulation device, comprising: a pair of electrodes configured to be electrically coupled to a user; and a wave generator configured to provide an electrical signal to the user via the pair of electrodes, wherein the wave generator is further configured to generate the electrical signal at one of a plurality of levels, each of the plurality of levels defined by at least a frequency, a peak voltage, and a peak current, and wherein for each of the levels: the peak current is in a range of about 25 mA-about 150 mA, and the frequency and the peak voltage have a generally inverse relationship.

Yet another aspect is a portable electrical stimulation device, comprising: a pair of electrodes configured to be electrically coupled to a user; and a wave generator configured to provide an electrical signal to the user via the pair of electrodes, the wave generator comprising a current limiter arranged in series with an output of the wave generator, wherein the wave generator is further configured to generate the electrical signal at one of a plurality of levels, each of the plurality of levels defined by at least a frequency, a peak voltage, and a peak current, and wherein for each of the levels: the frequency is in a range of about 50 Hz-about 500 Hz, and the peak voltage is in a range of about 40 V-about 250 V.

Still yet another aspect is a method of using a portable electrical stimulation device, comprising: placing a first electrode at a first location of a user; placing a second electrode at a second location of the user; selecting one of a plurality of levels for an electrical signal to be applied to the first and second electrodes via a wave generator, the wave generator configured to provide the electrical signal to the user via the pair of electrodes, wherein each of the plurality of levels is defined by at least a frequency, a peak voltage, and a peak current, and wherein the frequency and the peak voltage have a generally inverse relationship; and moving at least one of the first and second electrodes along a region of the user's skin while the electrical signal is provided to the first and second electrodes.

In certain embodiments, the method further comprises placing a third electrode and a fourth electrode on a third location of the user different from the first and second locations, wherein the moving the at least one of the first and second electrodes is performed while the electrical signal is provided to the third and fourth electrodes. In certain embodiments, the third location is feet of the user.

Another aspect is a method of using a portable electrical stimulation device, comprising: placing a first electrode at a first location of a first user; placing a second electrode at a second location of a second user; and selecting one of a plurality of levels for an electrical signal to be applied to the first and second electrodes via a wave generator, the wave generator configured to provide the electrical signal to the first user and the second user via the pair of electrodes, wherein each of the plurality of levels is defined by at least a frequency, a peak voltage, and a peak current, wherein the frequency and the peak voltage have a generally inverse relationship, and applying the electrical signal, with the wave generator, to the first and second electrodes while the second user is performing a massage on the first user, thereby forming an electrical path between the first and second electrodes via direct contact between the first and second users.

Yet another aspect is an electrical stimulation device, comprising: a wave generator configured to provide an electrical signal; and at least one electrode configured to output a stimulation pulse based on the electrical signal, wherein the wave generator is further configured to generate the electrical signal at one of a plurality of levels, each of the plurality of levels defined by at least a frequency, a peak voltage, and a peak current, and wherein for each of the levels: the frequency is in a range of about 50 Hz-about 500 Hz, the peak voltage is in a range of about 40 V-about 250 V, the peak current is in a range of about 25 mA-about 150 mA, and the frequency and the peak voltage have a generally inverse relationship.

In certain embodiments, the electrical stimulation device is portable or stationary.

In certain embodiments, the wave generator is wiredly or wirelessly connected to the at least one electrode.

In certain embodiments, the at least one electrode comprises one or more sensors configured to sense a user's reaction in response to the stimulation pulse having a first intensity level being applied to the user, and wherein the wave generator is configured to automatically adjust a level of the electrical signal to a second intensity level different from the first intensity level based on the sensed user's reaction.

In certain embodiments, the wave generator is configured to automatically adjust the level of the electrical signal to the second intensity level less than the first intensity level in response to the sensed user's reaction indicating that the user is feeling discomfort with the stimulation pulse having the first intensity level.

In certain embodiments, the at least one electrode comprises one or more sensors configured to sense a user's impedance in response to the stimulation pulse having a first intensity level being applied to the user, and wherein the wave generator is configured to automatically adjust a level of the electrical signal to a second intensity level different from the first intensity level based on the sensed user's impedance.

In certain embodiments, the wave generator is configured to automatically adjust the level of the electrical signal to the second intensity level greater than the first intensity level in response to the one or more sensors sensing no reaction by the user with the stimulation pulse having the first intensity level for a predetermined period of time.

In certain embodiments, the device further comprises a memory configured to store information regarding a user and a user's reaction to intensity levels.

In certain embodiments, the wave generator is configured to generate the electrical signal based on the information stored on the memory.

In certain embodiments, the at least one electrode comprises: a filter; a high density sponge placed over the filter; a flexible conductive contact placed over the high density sponge; a cover covering the flexible conductive contact; and an electrical wire connected to the flexible conductive contact.

In certain embodiments, the at least one electrode has one of the following shapes: a circular shape and a square shape.

BRIEF DESCRIPTION OF THE DRAWINGS

FIGS. 3A, 3B, 3C, 3D, and 3E are example circuit diagrams implementing portions of the block diagram of FIG. 2 in accordance with aspects of this disclosure.

DETAILED DESCRIPTION

In the following description, for purposes of explanation, numerous specific details are set forth in order to provide a thorough understanding of the various embodiments. It will be evident, however, to one of ordinary skill in the art that the various embodiments may be practiced without these specific details.

Overview of Portable Electrical Stimulation Device

As described in various example embodiments, a portable electrical stimulation device is described herein. Although the example embodiments are described with respect to a portable electrical stimulation device for the purpose of convenience of description, the described technology can be applied to a non-portable or stationary electrical stimulation device.

Figure 1A:
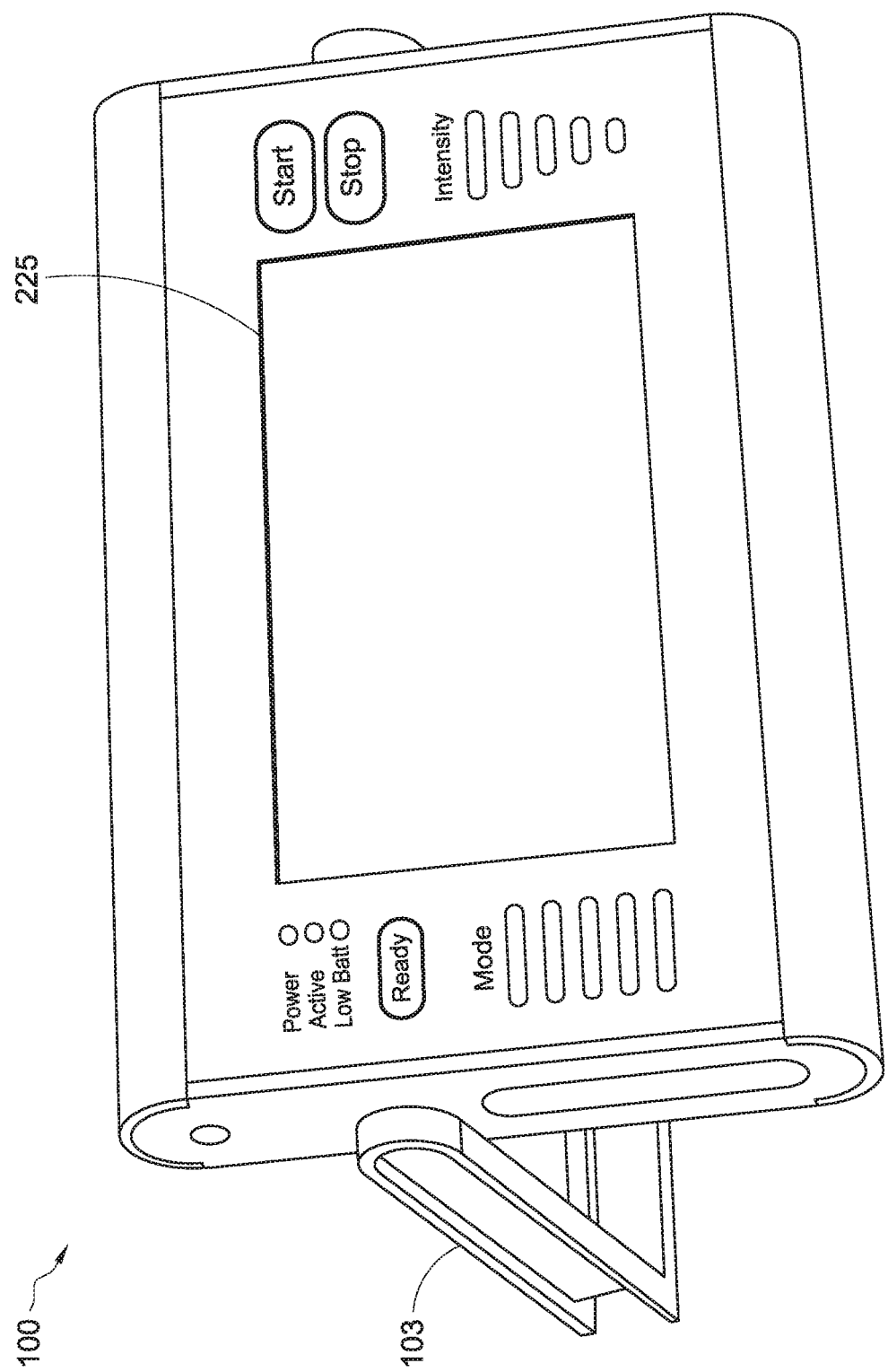
FIG. 1A is a perspective view illustrating an example portable electrical stimulation device in accordance with aspects of this disclosure.
Figure 1B:
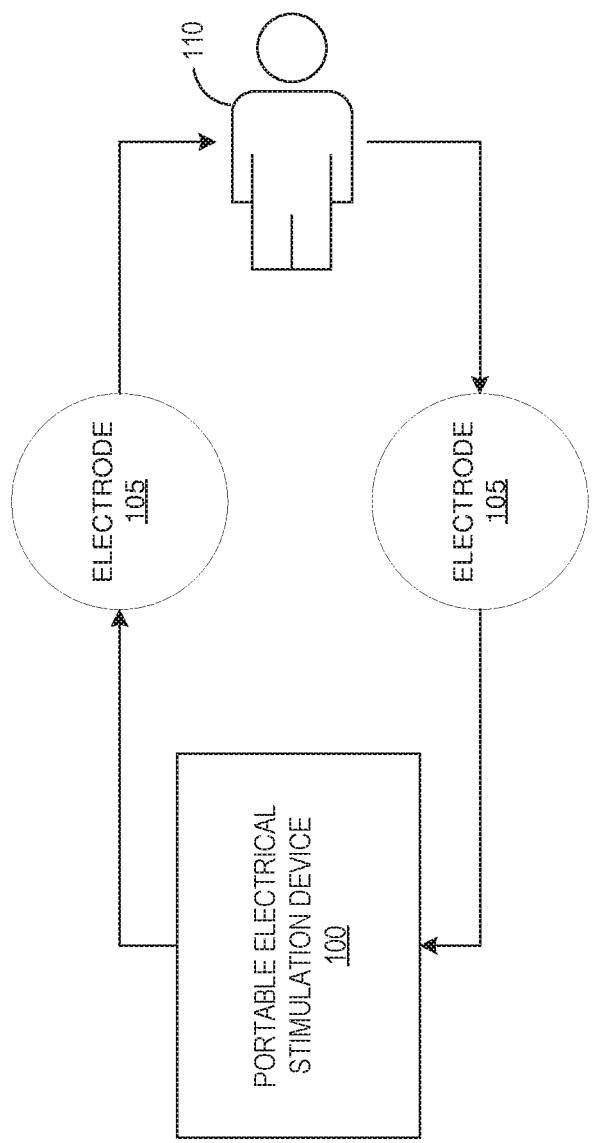
FIG. 1B is an example diagram illustrating how the portable electrical stimulation device of FIG. 1A can be connected to a user in accordance with aspects of this disclosure.

FIG. 1A is a perspective view illustrating an example portable electrical stimulation device 100 in accordance with aspects of this disclosure. FIG. 1B is an example diagram illustrating how the portable electrical stimulation device 100 of FIG. 1A can be connected to a user 110 in accordance with aspects of this disclosure.

With reference to FIG. 1A, the portable electrical stimulation device 100 can be embodied as a portable device comprising a user interface 225, a stand 103, and one or more connection ports (not illustrated) configured to be connected to external components and/or devices. The portable electrical stimulation device 100 shown in FIG. 1A is merely an example, and can have different structures, shapes, and/or user interfaces. Furthermore, certain components may be removed or others can be added to the portable electrical stimulation device 100. For example, the stand 103 may be removed and/or the user interface 225 may have different designs and/or arrangements of input touch pads/buttons. The user interface 225 may include an integrated touch LCD screen for user interface. The LCD screen may additionally include color changing LED indicators showing that the portable electrical stimulation device 100 is in a certain intensity level among multiple different intensity levels.

In some embodiments, the portable electrical stimulation device 100 may be wiredly or wirelessly connected to a user's portable communication device (not shown) such as a smartphone. In these embodiments, the smartphone may download a program or an application relating to the function of the user interface 225 so that the user may control the user interface via the smartphone.

As shown in FIG. 1B, the portable electrical stimulation device 100 can be coupled to one or more electrodes 105 configured to be placed on a user 110. The connection between the portable electrical stimulation device 100 and the electrodes 105 can be wired or wireless. During use, the electrodes 105 may be placed such that each of the electrodes 105 forms an electrical connection with the user's 110 skin. As described below in more detail, in some embodiments, one of the electrodes 105 may be stationary and the other electrode may be movable during use. In still other embodiments, both of the electrodes 105 may be moveable during use. In yet other embodiments, both of the electrodes 105 may be fixed during use. Furthermore, one of the electrodes 105 may be positioned in electrical contact with a first user's skin and the other electrode may be positioned on the skin of a second user who is treating the first user. In certain embodiments, the electrical conductivity between the user 110 and the electrodes 105 can be increased by providing a conductive or lubricant cream (not shown) between one or more of the electrodes 105 and the user's 110 skin. The conductive or lubricant cream can also provide user comfort during use.

The portable electrical stimulation device 100 can treat various target areas of body, including, but not limited to, feet, ankles, knees, calves, thighs, hip, shoulders, shoulder blades, lower back, biceps, tendons, muscle, scapula, skin, neck or glutes. Furthermore, knowledge of anatomy is not required for use by individual users, and the position of the electrodes 105 may not be critical for effective treatment in some embodiments. Various embodiments are advantageous over the standard TENS device at least in that the positioning of electrodes on a patient's body is critical to the effectiveness of the standard TENS device.

Figure 2:
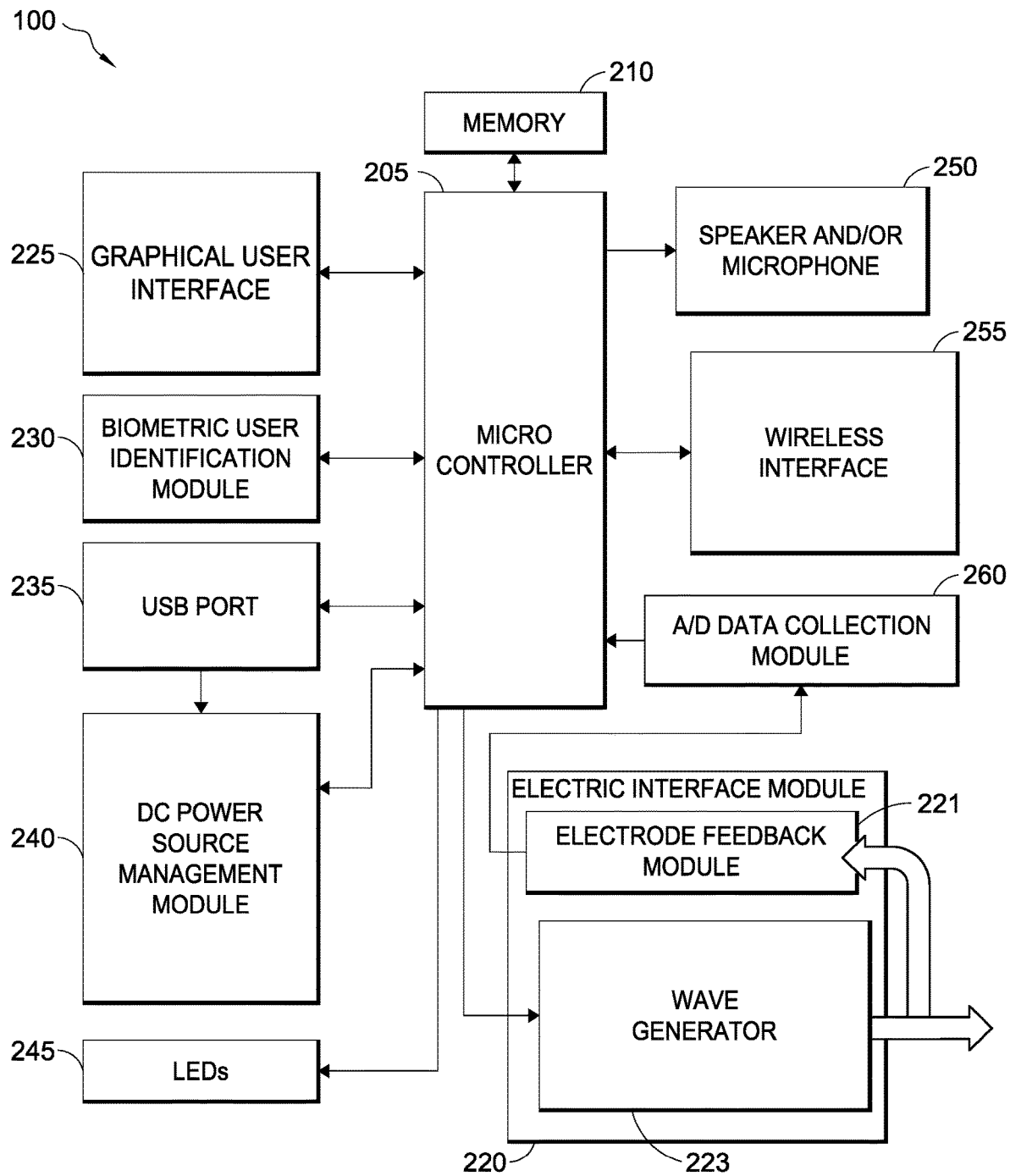
FIG. 2 is a block diagram illustrating an example of the components which can be included in the portable electrical stimulation device in accordance with aspects of this disclosure.

FIG. 2 is a block diagram illustrating an example of the components which can be included in the portable electrical stimulation device 100 in accordance with aspects of this disclosure. For example, in the embodiment of FIG. 2, the portable electrical stimulation device 100 includes a microcontroller 205 (which in certain implementations, may be embodied as one or more microcontrollers), a memory 210, an electrode interface module 220, a graphical user interface 225, a biometric user identification module 230, a universal serial bus (USB) port 235, a DC power source management module 240, LEDs 245, a speaker and/or microphone 250, a wireless interface 255, and an analog/digital data collection module 260. In certain embodiments, the portable electrical stimulation device 100 may include a voice activation module (not illustrated) which may be implemented as a separate module and/or implemented via software running on the microcontroller 205 using the microphone 250 as an input. FIG. 2 is merely an example of the portable electrical stimulation device 100, and the portable electrical stimulation device 100 can have many different configurations. For example, one or more of the illustrated blocks may be omitted from the portable electrical stimulation device 100, one or more additional blocks may be added to the portable electrical stimulation device 100, two or more blocks combined and/or one block can be separated into multiple blocks.

The electrode interface module 220 includes an electrode feedback module 221 and a wave generator 223. As described herein, the wave generator 223 is configured to generate an electrical signal to be provided to the user 110 via the electrodes 105. Accordingly, the electrode interface module 220 may be configured to electrically connect the electrodes 105 to the wave generator 223. In certain embodiments, the wave generator 223 is further configured to generate the electrical signal at one of a plurality of levels. Each of the levels may be defined by one or more of the following parameters: a frequency, a peak voltage, wave shape, and a current. The electrode feedback module 221 may receive a feedback signal indicative of one or more of the parameters of the electrical signal provided to the user 110.

FIGS. 3A, 3B, 3C, 3D, and 3E are example circuit diagrams implementing portions of the block diagram of the portable electrical stimulation device 100 of FIG. 2 in accordance with aspects of this disclosure. The circuit diagrams shown in FIGS. 3A-3E are merely examples, and other circuit configurations can also be used. Furthermore, certain circuit components may be removed or others can be added to the circuit diagrams shown in FIGS. 3A-3E. As shown in FIGS. 3A-3E, the portable electrical stimulation device 100 may include the USB port 235, the microcontroller 205, a battery charger module 310, a regulator 315, a battery connector 320, a programming/debugging port 325, a testing port 330, one or more timing crystals 335, an expansion port 340, one or more LEDs 345, one or more control switches 350, and an electrical output circuit 355.

Figure 3A:
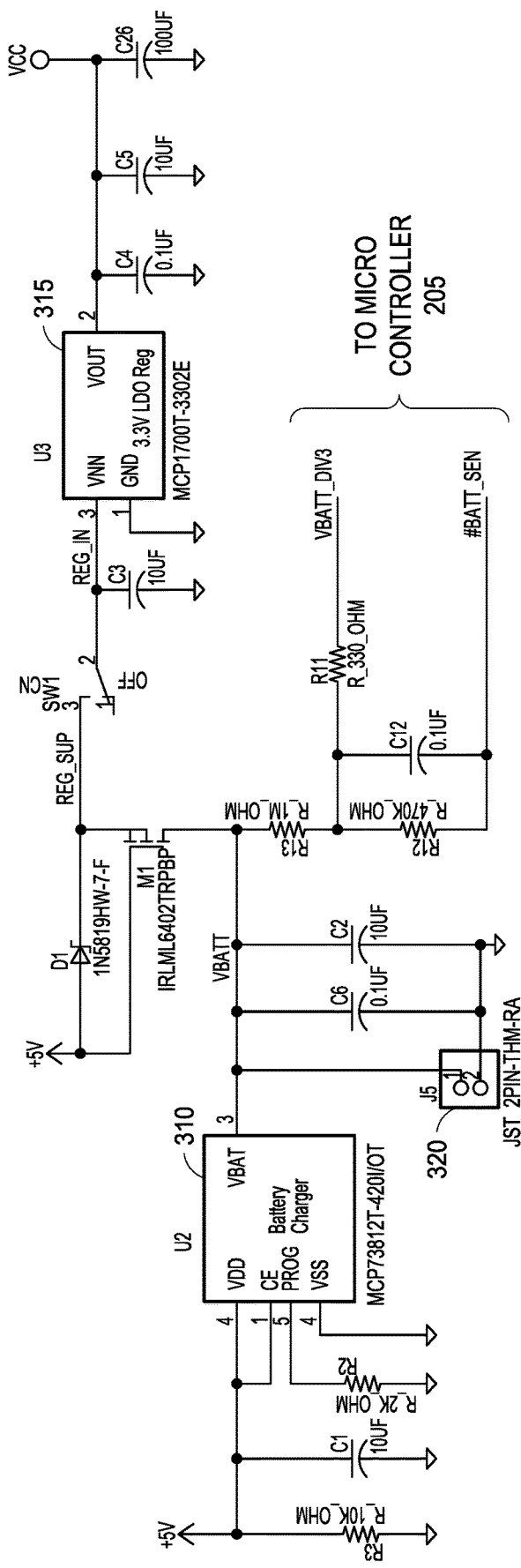

Referring to FIGS. 3A and 3B, the USB port 235 may be configured to connect to an external USB charger to provide power to the portable electrical stimulation device 100. In certain embodiments, the microcontroller 205 may be configured to communicate with external devices (e.g., a computer, mobile phone, another portable electrical stimulation device 100, a feedback device, etc.) via the USB port 235. Thus, certain lines from the USB port 235 may be electrically connected to the microcontroller 205. The battery charger 310 may be configured to charge a battery (not illustrated) connected to the battery connector 320 when USB power is received from the USB port 235. Depending on whether the portable electrical stimulation device 100 is powered from the USB port 235 or the battery, the regulator 315 may be configured to step up and/or step down the voltage received from the USB port 235 or the battery to a voltage used by other components of the portable electrical stimulation device 100. In some embodiments, a series boost circuit may be used to produce the regulator input when driven by a source lower than, for example, 3.3V. Other embodiments may use a low dropout regulator that produces, for example, 3.3V when supplied with 3.3V or more. Although not shown, the electrical stimulation device 100 may also be powered by an electrical power outlet (e.g., 100V-240V) using a power AC-DC adapter, in addition to or instead of the USB port 235. In certain embodiments, the regulator 315 can step down a 5 V power voltage to 3.3 V used by certain components.

Figure 3C:
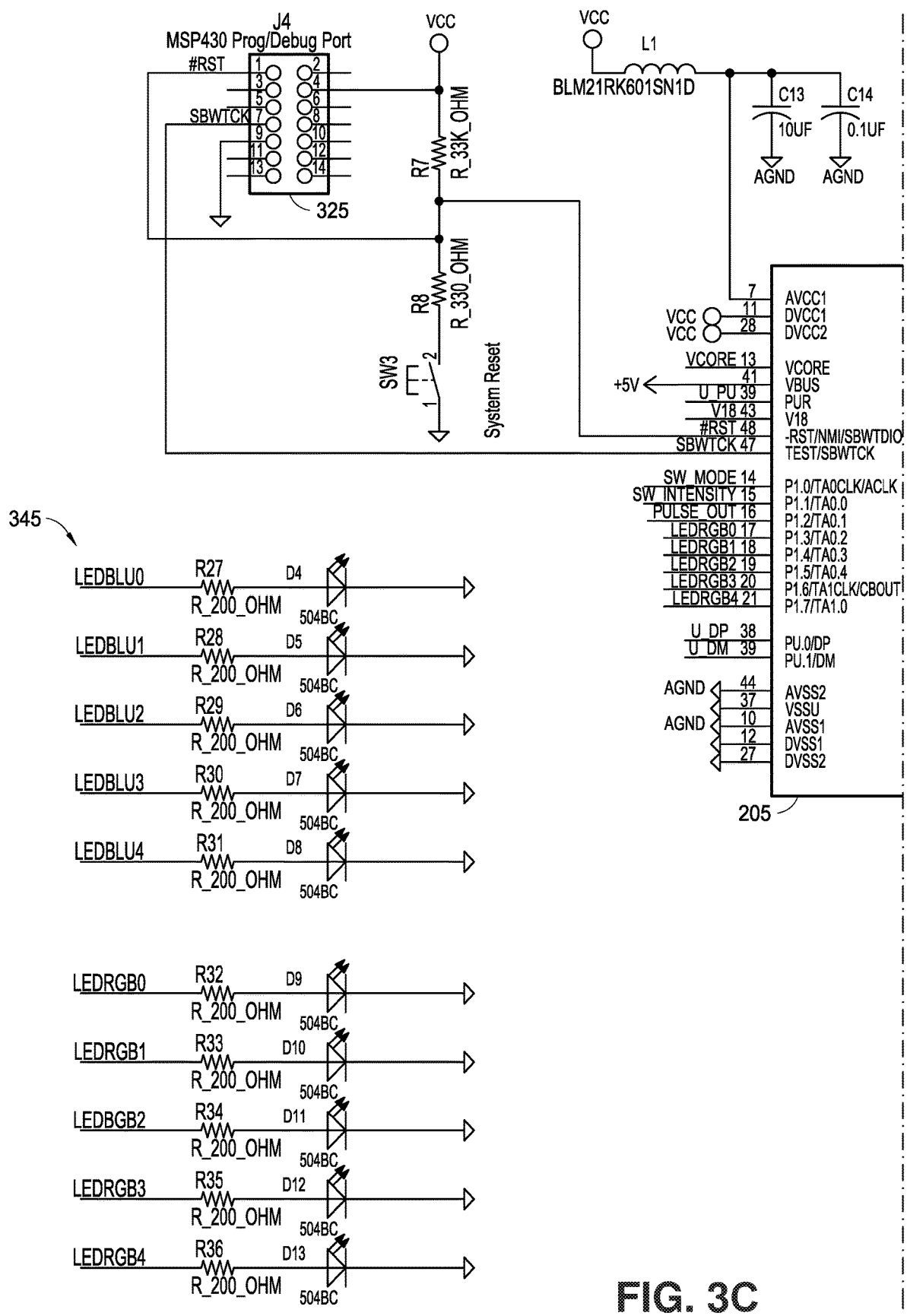
Figure 3D:
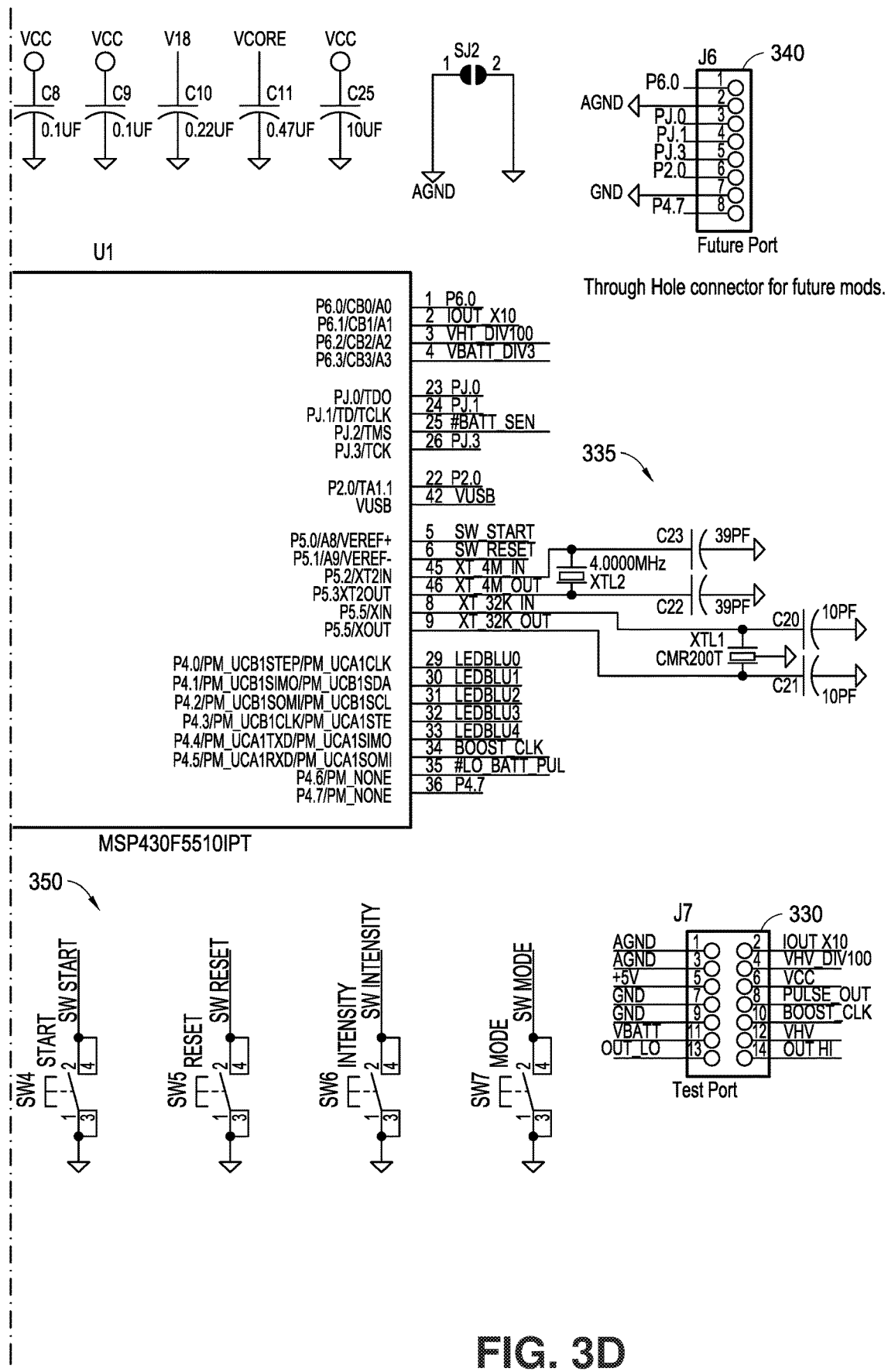

FIGS. 3C and 3D are connected by the dashed line and illustrate that the microcontroller 205 may be configured to connect to other internal and/or external components via one or more ports 325, 330, and 340. These ports 325, 330, and 340 may be configured to allow for reconfiguration of the microcontroller 205. In addition to providing output via the graphical user interface 225, the microcontroller 205 may be configured to provide output via the LEDs 345 and receive control input via the control switches 350. The microcontroller 205 may also use input received from the timing crystals 335 to generate control signals, such as a boost clock signal, used to generate the electrical signal provided to the electrodes 105. It should be appreciated that in certain embodiments, one or more of the ports 325, 330, and 340, LEDs 345, switches 350, and timing crystals 335 may be omitted and/or implemented using other components.

Figure 3E:
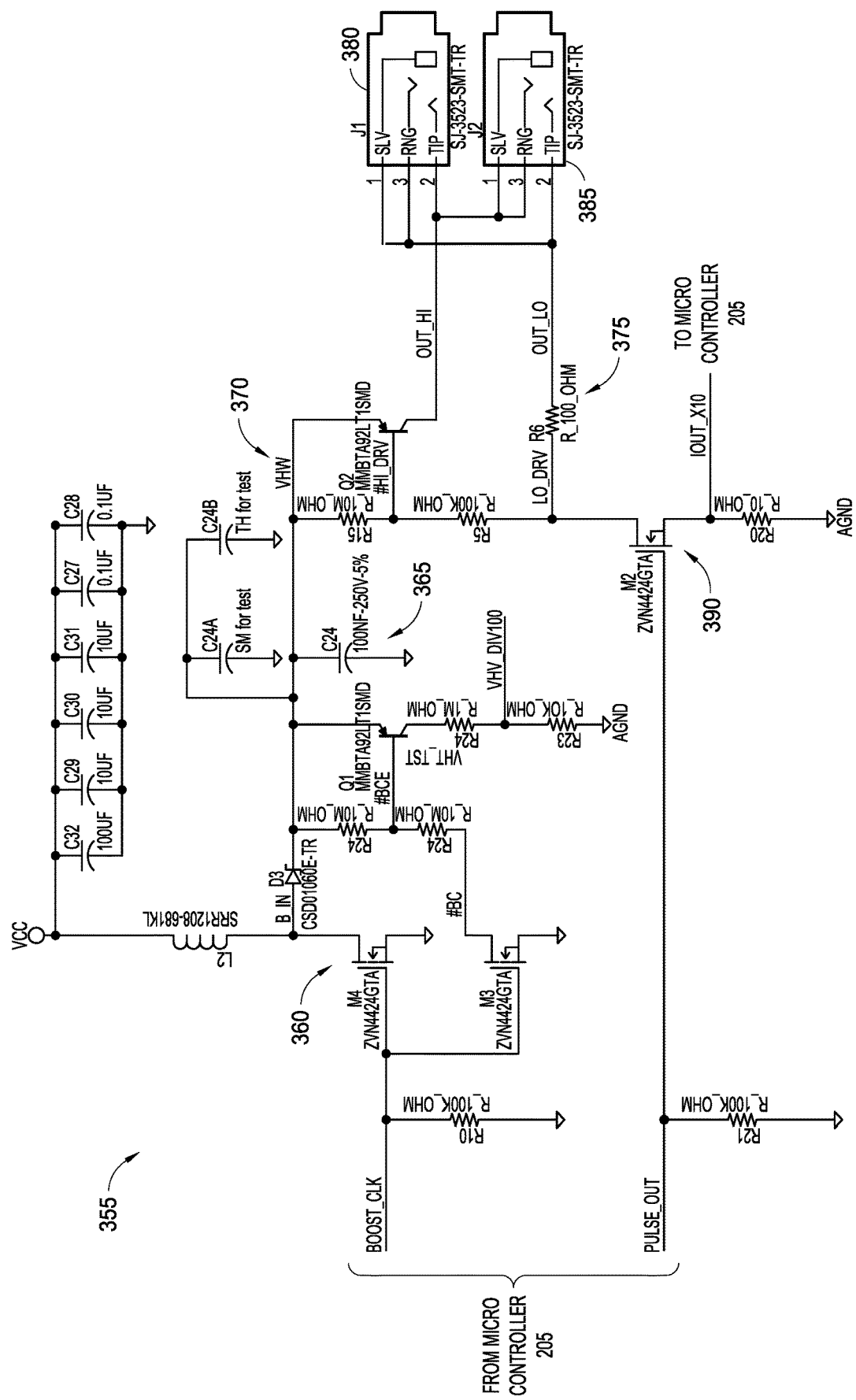

Referring to FIG. 3E, the electrical output circuit 355 may be configured to receive the boost clock signal BOOST_CLK and a pulse out signal PULSE_OUT from the microcontroller 205 and output the electrical signal to the electrodes 105 via a high electrode port 380 and a low electrode port 385. In certain embodiments, the electrical output circuit 355 may be configured as a boost converter to boost the signal provided by the boost clock signal. The boost clock signal BOOST_CLK and the pulse out signal PULSE_OUT may be generated by the microcontroller 205 to control generation of the electrical signal provided to the electrodes 105. The pulse out signal PULSE_OUT may be high during generation and/or application of a therapy pulse to the electrodes 105. The boost clock signal BOOST_CLK may be cycled high and low during active therapy to generate the electrical signal having pulses at the desired level. Both of the boost clock signal BOOST_CLK and the pulse out signal PULSE_OUT may be low when not providing electrical therapy.

For example, a transistor 360 (e.g., an MOS switch transistor) may be configured to be switched on so as to draw current from the power supply rail Vcc through an inductor L2 when the boost clock signal BOOST_CLK is high. For example, the transistor 360 may be configured to sink current to ground through the inductor L2 while the boost clock signal BOOST_CLK is high, and once the boost clock signal BOOST_CLK switched to low, the energy from the inductor L2 may be transferred to one or more capacitors 365 where the current is stored prior to being provided to the electrode ports 380 and 385. In some embodiments, the one or more capacitors 365 may include one or more additional capacitors arranged in series and/or in parallel (e.g., capacitors C24A, C24B) to adjust the capacitance of the capacitors 365, thereby affecting the amount of energy which can be stored on the one or more capacitors 365, at a given voltage.

The microcontroller 205 can control the voltage generated on the line 370 (also referred to as the VHV voltage) by adjusting the boost clock signal. In certain embodiments, the boost clock signal may be a square wave or a pulse wave (also referred to as a pulse train) adjustable by the microcontroller 205. For example, the microcontroller 205 may be configured to adjust one or more of the following parameters of the boost clock signal: the duty cycle (e.g., via the positive pulse width), the number of pulses applied, a feedback signal (illustrated as VHV_DIV100 in FIG. 3E) provided to the microcontroller, frequency, positive pulse width, neutral pulse width, etc. Since the capacitor 365 is coupled to the power supply rail Vcc via the inductor L2, the voltage applied to the capacitor 365 may increase during a ramp up period after the transistor 360 is activated by the boost clock signal. Thus, a longer positive pulse width on the boost clock signal may result in a higher voltage signal supplied to the capacitor 365.

The microcontroller 205 can generate a pulse wave that drives the gate of the transistor 360 whose drain is electrically connected to the supply voltage VCC (e.g., which may be a 3.3V supply). The microcontroller 205 generated boost clock pulse wave can be used to switch the input of the boost circuit to charge the capacitor 365 to a desired level. The boost clock may be then disabled and the energy stored in the capacitor 365 may be used to create a therapy pulse. The energy stored in the capacitor 365 may be a function of the number of boost clock cycles applied by the microcontroller 205 to the capacitor 365. Thus, voltage regulation can be done by controlling the number of boost clock cycles and the duty cycle of the boost clock through the microcontroller 205. In other embodiments, the microcontroller 205 can generate electrical signals having a shape other than a square wave or a pulse wave. For example, in certain embodiments the microcontroller 205 can generate non-rectangular wave such as a sine wave, a triangular wave, etc.

The energy stored on capacitor 365 can be supplied to the electrodes 105 (and thus to the user 110) via the electrode ports 380 and 385. The microcontroller 205 can control application of the energy stored on the capacitor 365 to the electrode ports 380 and 385 via the pulse out signal provided to a transistor 390. In addition, part of the electrical signal received back from the user 110 through the low electrode port 385 can be provided to the microcontroller 205 as a feedback signal IOUT_X10 (see the left side of the text "TO MICROCONTROLLER 205" in FIG. 3E) used to measure the electrical signal. In certain embodiments, the feedback signal IOUT_X10 is provided to the electrode feedback module 221 and the analog/digital data collection module 260 before being provided to the microcontroller 205.

The electrical output circuit 355 may further include a current limiting component 375 arranged in series with at least one of the electrode ports 380 and 385. In certain embodiments, the current limiting component 375 is embodied as one or more resistive elements arranged in series prior to the output to the electrodes 105, which function to limit the amount of current output. In other embodiments, the current limiting component 375 can be made with other circuits such as negative temperature coefficient (NTC) thermistors. The microcontroller 205 or an additional processor (not shown) of the portable electrical stimulation device 100 can also limit the amount of current output by software. The current limiting elements may improve the safety of the portable electrical stimulation device 100 and prevent the higher levels from delivering too much power to the user 110, which may be uncomfortable to the user 110.

Figure 4A:
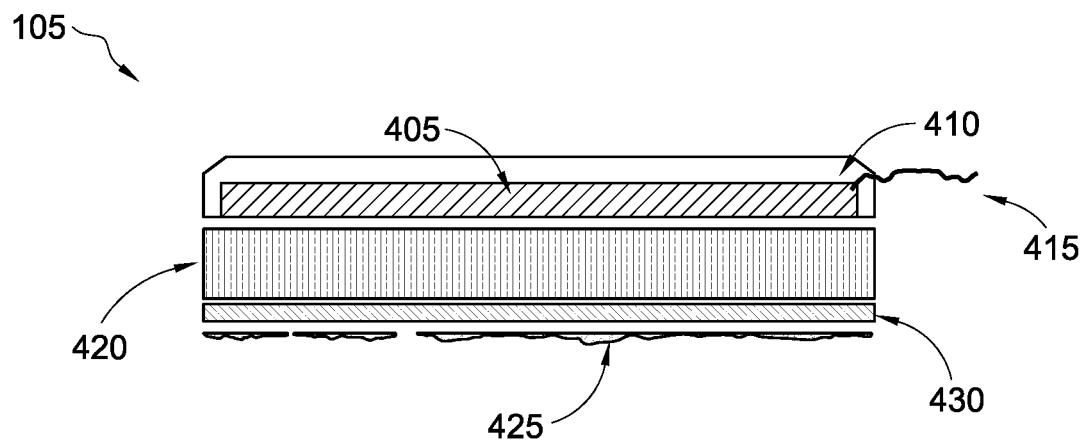
FIGS. 4A, 4B, 4C and 4D are views of example embodiments of the electrodes illustrated in FIG. 1B in accordance with aspects of this disclosure.
Figure 4B:
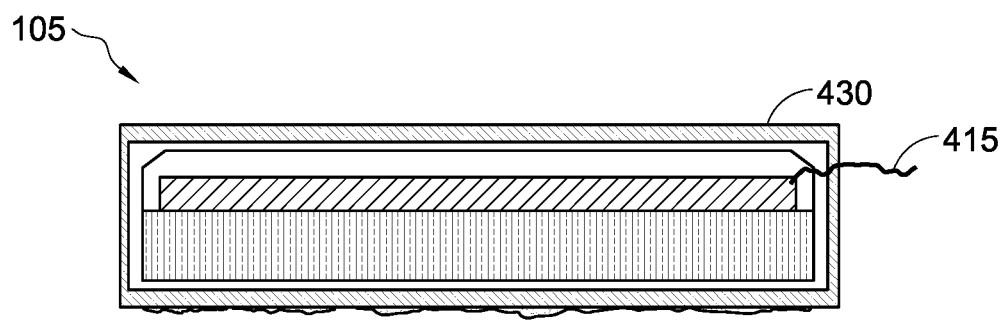
Figure 4C:
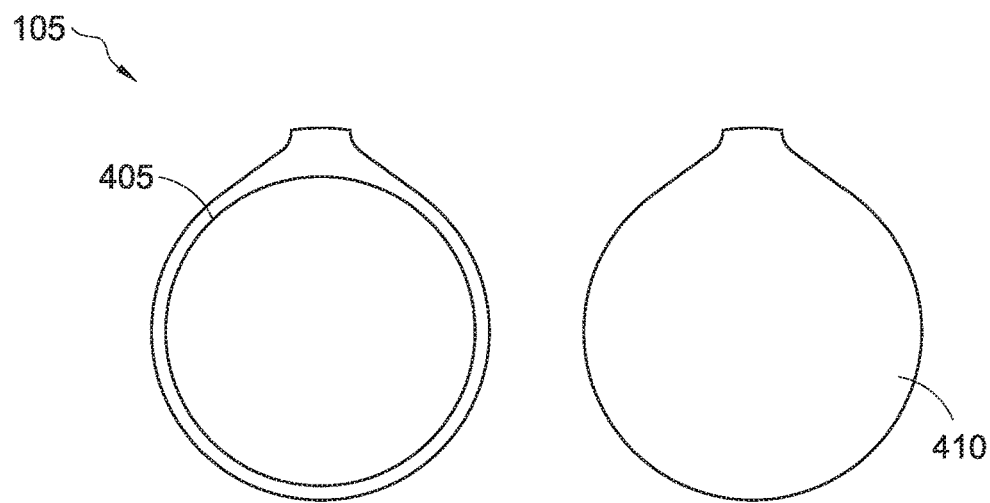
Figure 4D:
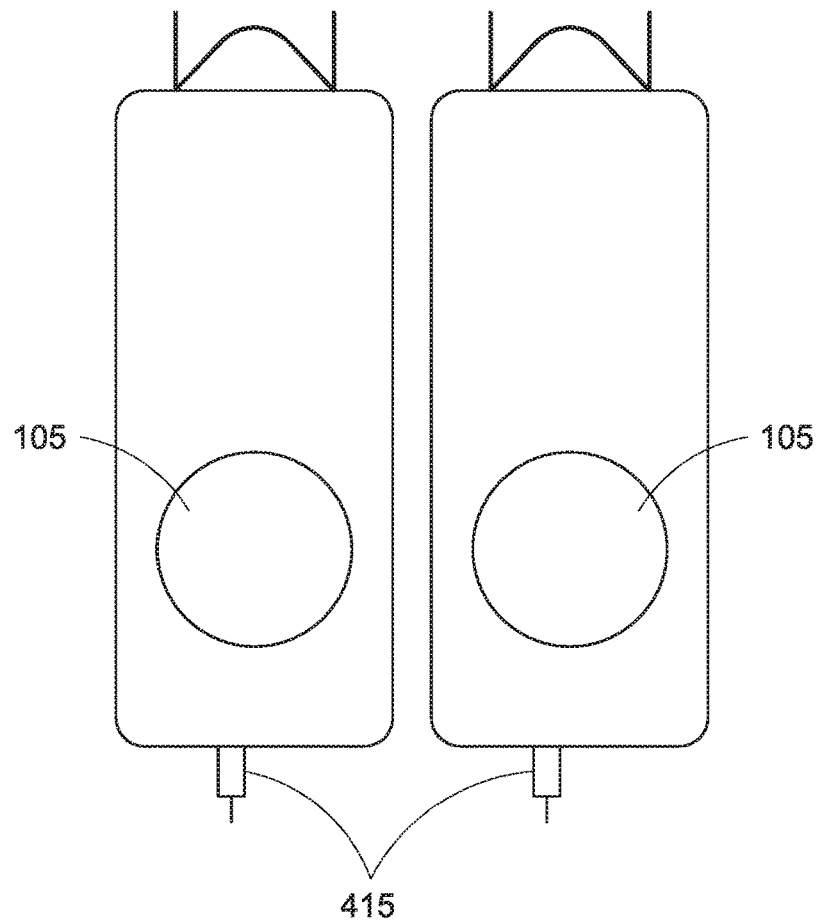

FIGS. 4A, 4B, 4C and 4D are views of example embodiments of the electrodes illustrated in FIG. 1B in accordance with aspects of this disclosure. As shown in FIGS. 4A, 4B and 4C, the electrode 105 includes flexible conductive contact 405, a cover 410, an electrical wire 415, a high density sponge 420, and a cover 430. In some embodiments, the cover 430 comprises a wet paper towel or "tea bag" filter, however, the detailed description is not limited thereto. In certain embodiments, the flexible conductive contact 405 may be formed of a conductive graphite and the cover 410 may be formed of silicone. A conductive cream 425 may also be applied to the cover 430 before the electrode 105 is attached to the user's 110 skin. The conductive cream 425 may improve electrical conductivity between the electrodes 105 and the user's 110 skin and/or can be used as lubricant cream that provides comfort to the use 110, particularly, when one of the electrodes 105 is moving. In embodiments where the electrodes 105 are attached to the user's 100 feet, the high density sponge 420 and the conductive cream 425 may be omitted from the electrode 105. FIG. 4D illustrates an embodiment of the electrodes 105 which can be used as foot pads without the high density sponge 420 and the conductive cream 425. In FIG. 4D, reference numeral 415 represents an electrical wire. As shown in FIGS. 4A, 4B, 4C and 4D, the electrode 105 may have one of the following shapes: a circular shape or a square shape. However, the shape of the electrode 105 is not limited thereto and in other embodiments, the electrode 105 may have various other shapes (e.g., polygonal shapes).

In certain embodiments, at least one of the electrodes 105 may also include one or more sensors configured to sense biometric parameters of the user 110 before and/or during treatment. The sensors may sense a user's impedance, other body characteristic or physical reaction (e.g., sudden movement or shaking) in response to a first intensity level due to a higher intensity than expected by the user. The microcontroller 205 may use the measured parameters to automatically adjust the level of the generated electrical signal based on a model of the user's 110 response to the electrical signal. For example, the microcontroller 205 can automatically adjust the intensity level to a second intensity level lower than the first intensity level. As another example, if the sensors sense no reaction (e.g., the measured reaction is less than a threshold level) from a user who is receiving treatment in a first intensity level for a predetermined period of time, the microcontroller 205 can automatically adjust the intensity level to a second intensity level higher than the first intensity level. The sensing and automatic intensity level adjustment can be user configurable, for example, with respect to the length of the predetermined time and/or the intensity level to be changed from an initial intensity level. Furthermore, the user configurable information and/or setting can be saved in the memory 210 for future uses by specific individuals. In other embodiments, the user configurable information and/or setting can be saved in a network system such as a cloud database or user's mobile terminal for communicating with the portable electrical stimulation device 100.

In certain embodiments, the microcontroller 205 can recognize a user's voice command received through the microphone 250 (see FIG. 2) in connection with operations of the portable electrical stimulation device 100 such as turning on/turning off the device, timer duration, intensity level changes, etc. For example, if the user's voice command is to change an intensity level from a first level to a second different level, the microcontroller 205 can control the wave generator 223 to change the intensity level from the first level to the second different level.

Parameters of the Electrical Signal

In certain embodiments, the microcontroller 205 is configured to generate the electrical signal at one of a plurality of intensity levels. Each of the levels can be defined by parameters including at least a frequency, a peak voltage, and/or a current. In certain embodiments, the microcontroller 205 may be configured to allow for the selection of one of five levels, having parameters defined by table 1 below.

TABLE 1

| Level | Frequency (Hz) | Peak Output Voltage | | Active Pulse | |
|---|---|---|---|---|---|
| | | No Load (V) | Body Load (V) | Width (ms) | Period (ms) |
| 1 | 328.5 | 92 | 56 | 2.000 | 3.044 |
| 2 | 250.6 | 128 | 77 | 2.000 | 3.990 |
| 3 | 183.4 | 147 | 103 | 2.000 | 5.453 |
| 4 | 98.23 | 163 | 147 | 2.000 | 10.18 |
| 5 | 60.13 | 210 | 156 | 2.000 | 16.63 |

The peak current for the above levels may vary between about 5 mA to about 250 mA and may be determined based on the peak voltage Vmax parameter and the current resistance of the user 110 between the electrodes 105. The average current for the above levels may vary between about 1 mA to about 15 mA. Thus, in certain embodiments, for each of the levels: the frequency can be in a range of about 50 Hz to about 500 Hz, the peak voltage can be in a range of about 40 V to about 250 V, the peak current can be in a range of about 5 mA to about 250 mA. The frequency can also be in a range of about 60 Hz to about 400 Hz, about 70 Hz to about 350 Hz, or about 80 Hz to about 300 Hz, or any other frequency ranges within the range of about 50 Hz to about 500 Hz. The peak voltage can be in a range of about 60 V to about 200 V, about 70 V to about 180 V, or about 80 V to about 160 V, or any other voltage ranges within the range of about 50 V to about 250 V. Additionally, the peak voltage may vary according to the load presented to the wave generator 223 by the user 110 and/or if the electrodes 105 are not connected to the user 110. The values illustrated in Table 1 may be an example of the peak load measured for an example body load of a user 110, which may vary depending on the user 110.

Figure 5A:
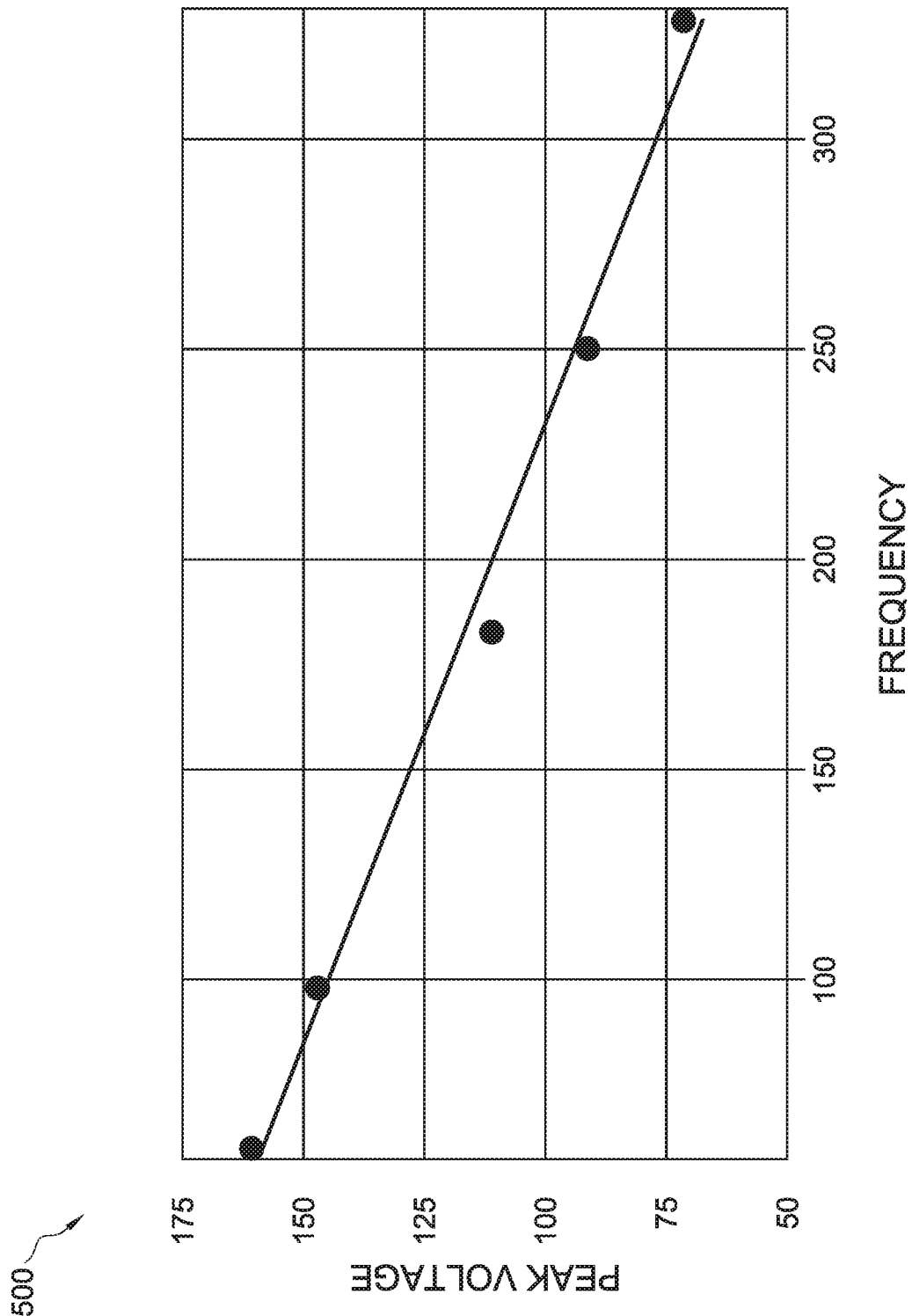
FIG. 5A is an example graph illustrating the relationship between the peak voltage and the frequency over a plurality of levels generated by the portable electrical stimulation device in accordance with aspects of this disclosure.

The peak current can be in a range of about 5 mA to about 250 mA, about 10 mA to about 175 mA, about 25 mA to about 150 mA, or any other peak current ranges within the range of about 5 mA to about 250 mA. The average current can be in a range of about 1 mA to about 15 mA, about 2.5 mA to about 7.5 mA, about 4 mA to about 6 mA, or any other peak current ranges within the range of about 1 mA to about 15 mA. Additionally, the frequency and the peak voltage can have a generally inverse relationship in which the peak voltage generally increases as the level increases and the frequency generally decreases as the level increases, as shown in FIG. 5A. The intensity levels can be less or more than five (e.g., three, seven, or any integer or other non-integer value). Furthermore, the numbers shown in Table 1 are merely example numbers and can have different numbers as long as the frequency and the peak voltage have a generally inverse relationship and/or the frequency, peak voltage and current satisfy the above described ranges.

Although not shown in Table 1, the root-means-square (RMS) voltage may be relatively stable across the levels, and the overall power delivered may be limited (with a hard or soft cap) by the current limiting element 375 or current limiting software described above. Additionally, in certain embodiments, the positive pulse width is static regardless of the levels when measured with an open circuit between the electrodes 105. Accordingly, the microcontroller 205 may be configured to adjust the neutral pulse width to achieve the frequency for the selected level. The microcontroller 205 may be configured to generate strictly positive pulses. In other embodiments, the microcontroller 205 may be configured to generate waves having substantially equal active pulse widths (e.g., at least one of the active pulse may not necessarily be positive) by altering the period of the generated waves.

The user's 110 body may adapt to the electrical signals being applied by the portable electrical stimulation device 100. Thus, it may be desirable to adjust the level being applied during treatment. The portable electrical stimulation device 100 may be configured to receive control input to switch between the levels (e.g., a selection of one of levels 1-5) via the control switches 350 or another user interface such as graphical user interface 225 of microphone 250. While the portable electrical stimulation device 100 switches between two levels, there may be a short period of inactivity in which no electrical signal is applied to the user 110. Thus, the user 110 may experience a "shock," and/or discomfort if the full voltage of the newly selected level is applied substantially instantaneously to the user 110. In certain embodiments, the portable electrical stimulation device 100 may be configured to gradually increase the Vmax parameter when transitioning to the newly selected level, to minimize such discomfort and/or shock from occurring. The portable electrical stimulation device 100 may generate this transition by ramping and/or stepping the system up to the selected level by applying parameters (e.g., the peak voltage Vmax) which are represented by sub-levels in between the above-indicated table of levels.

Figure 5B:
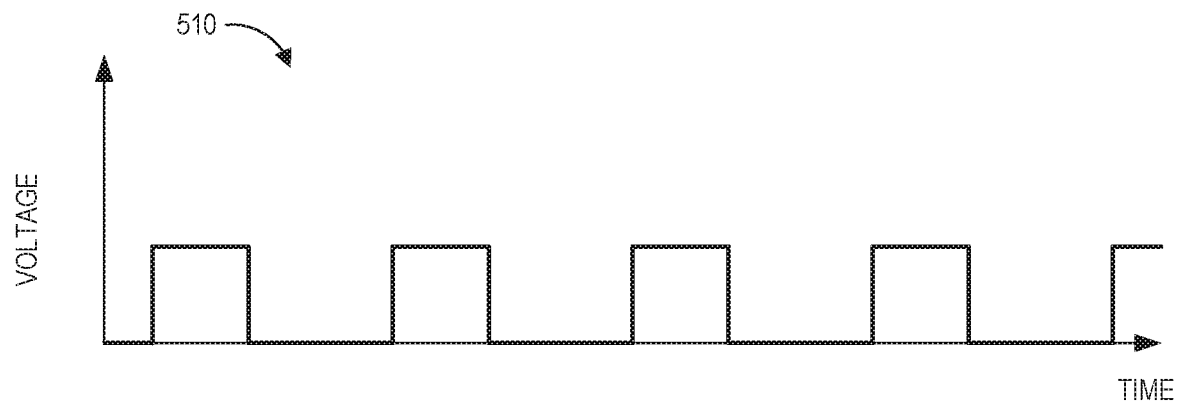
FIGS. 5B and 5C are graphs illustrating example waveforms which may be generated by the wave generator of the portable electrical stimulation device in accordance with aspects of this disclosure.
Figure 5C:
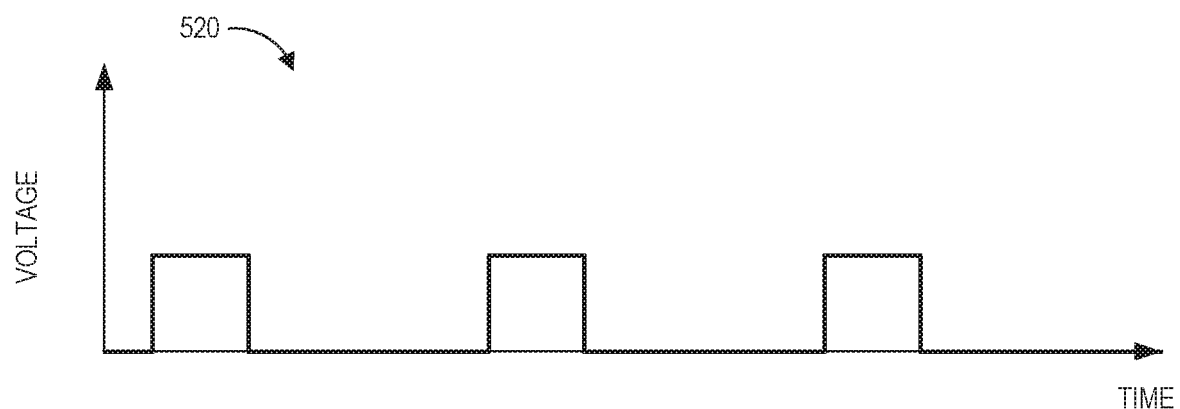

FIGS. 5B and 5C are graphs illustrating example waveforms which may be generated by the wave generator 223 of the portable electrical stimulation device 100 in accordance with aspects of this disclosure. In certain embodiments, the waveforms 510 and 520 illustrated in FIGS. 5B and 5C may correspond to the electrical signal output to the electrodes 105. Although the waveforms 510 and 520 are illustrated as pulse waves in FIGS. 5B and 5C, aspects of this disclosure are not limited thereto. For example, the specific waveform applied to the user 110 may depend on the load presented to the electrodes 105 when connected to the user 110, which may depend on, for example, the resistance of the user 110 during application of the electrical signal, the placement of the electrodes 105 on the user 110, and/or whether the conductive cream 425 is used, etc.

As shown in FIGS. 5B and 5C, each of the waveforms 510 and 520 generated by the portable electrical stimulation device 100 may have substantially the same positive pulse width. Thus, in order to adjust the frequency between the waveform 510 and the waveform 520, the portable electrical stimulation device 100 may adjust the neutral pulse width. Although the term neutral pulse width may be used to describe the period in which a positive pulse is not applied to the electrodes 105, the portable electrical stimulation device 100 may provide an electrical signal having a voltage of about 0 V, rather than a strictly negative pulse. Although not specifically illustrated, the portable electrical stimulation device 100 may adjust the voltage of the neutral pulse width according to the selected level in addition to adjusting the neutral pulse width to set the frequency.

Figure 5D:
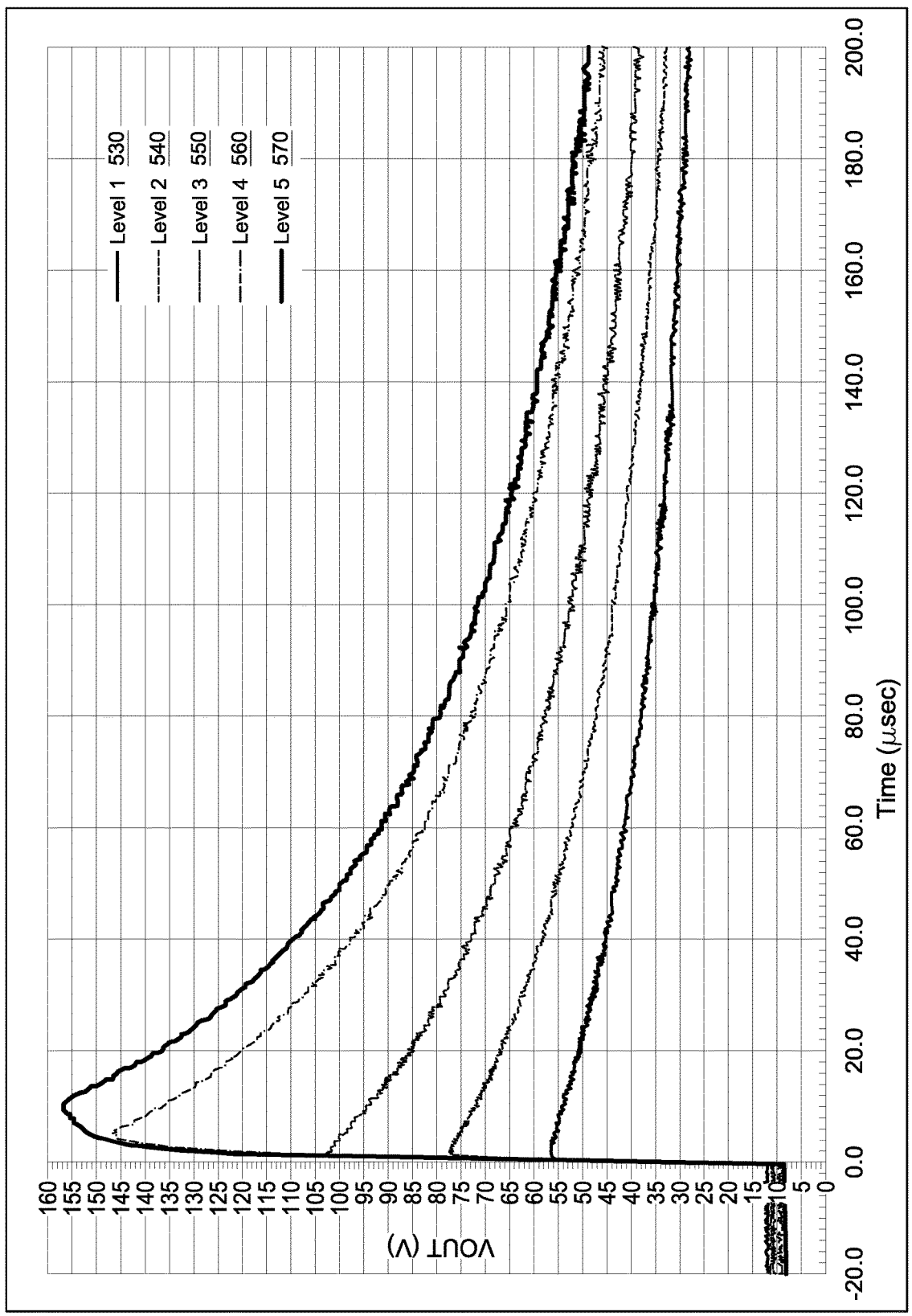
FIG. 5D is a graph illustrating additional example waveforms which may be generated by the wave generator of the portable electrical stimulation device in accordance with aspects of this disclosure.

FIG. 5D is a graph illustrating additional example waveforms 530-570 which may be generated by the wave generator 223 of the portable electrical stimulation device 100 in accordance with aspects of this disclosure. In particular, FIG. 5D illustrates an example waveform 530 produced at level 1, an example waveform 540 produced at level 2, an example waveform 550 produced at level 3, an example waveform 560 produced at level 4, and an example waveform 570 produced at level 5, when the electrical signal is applied to the user 110 acting as a load. In certain embodiments, the load presented by the user 110 may be in the range of about 0.5 kΩ to about 6 kΩ, or, in the range of about 3 kΩ to about 4 kΩ. Of course, the load presented by the user 110 may not be strictly resistive and may include a capacitive component forming an impedance value.

As shown in FIG. 5D, the waveforms 530-570 may quickly approach a peak value as the capacitor 365 is unloaded through the electrodes 105. For an example load of 2.2 kΩ, the electrical circuit formed between the portable electrical stimulation device 100 and the user 110 may have an IR time constant of about 0.3 ns and an RC time constant of about 1.3 μs. The capacitor 365, the capacitance of the user 110, along with any other sources of parasitic capacitance and/or inductance result in a ramp up of the waveforms 530-570 to the peak value, within about 1 μs to about 20 μs, depending on the level being produced by the portable electrical stimulation device 100. In other embodiments, the ramp up of the waveforms 530-570 to the peak value may be less than about 1 μs or greater than about 20 μs. The amount of time required to reach the peak voltage value may increase with increasing level. As shown in FIG. 5D, the voltage of the waveforms 530-570 drop off from the peak value and decay as the energy stored in the capacitor 365 is applied to the user 110 through the electrodes 105.

Use Modes

The portable electrical stimulation device 100 may be used in a plurality of different use modes. FIG. 1B illustrates a certain embodiment of use modes in which two electrodes 105 are applied to the skin of the user 110. In a first use mode, the electrodes 105 may be placed in stationary positions on the user 110 throughout a session of use of the portable electrical stimulation device 100. In a second use mode, a first one of the electrode 105 may be placed in a stationary position while the user 110 or another user moves a second one of the electrode 105 over a region of the user's 110 body. In certain embodiments, the user 110 may place the electrodes 105 on their body. Since cream can be applied to the electrodes 105, it may not be desirable for the user 110 to touch the portable electrical stimulation device 100 to adjust the currently applied level of the electrical signal being generated by the portable electrical stimulation device 100. As described above, the portable electrical stimulation device 100 may include the microphone 250 and voice recognition system (e.g., which may be implemented by the microcontroller 205) which can be configured to receive voice commands from the user 110 to operate the portable electrical stimulation device 100. Accordingly, the user 110 may be able to adjust the level of the portable electrical stimulation device 100, or input other commands to the portable electrical stimulation device 100, while the user 110 is positioning the electrodes 105.

Figure 6:
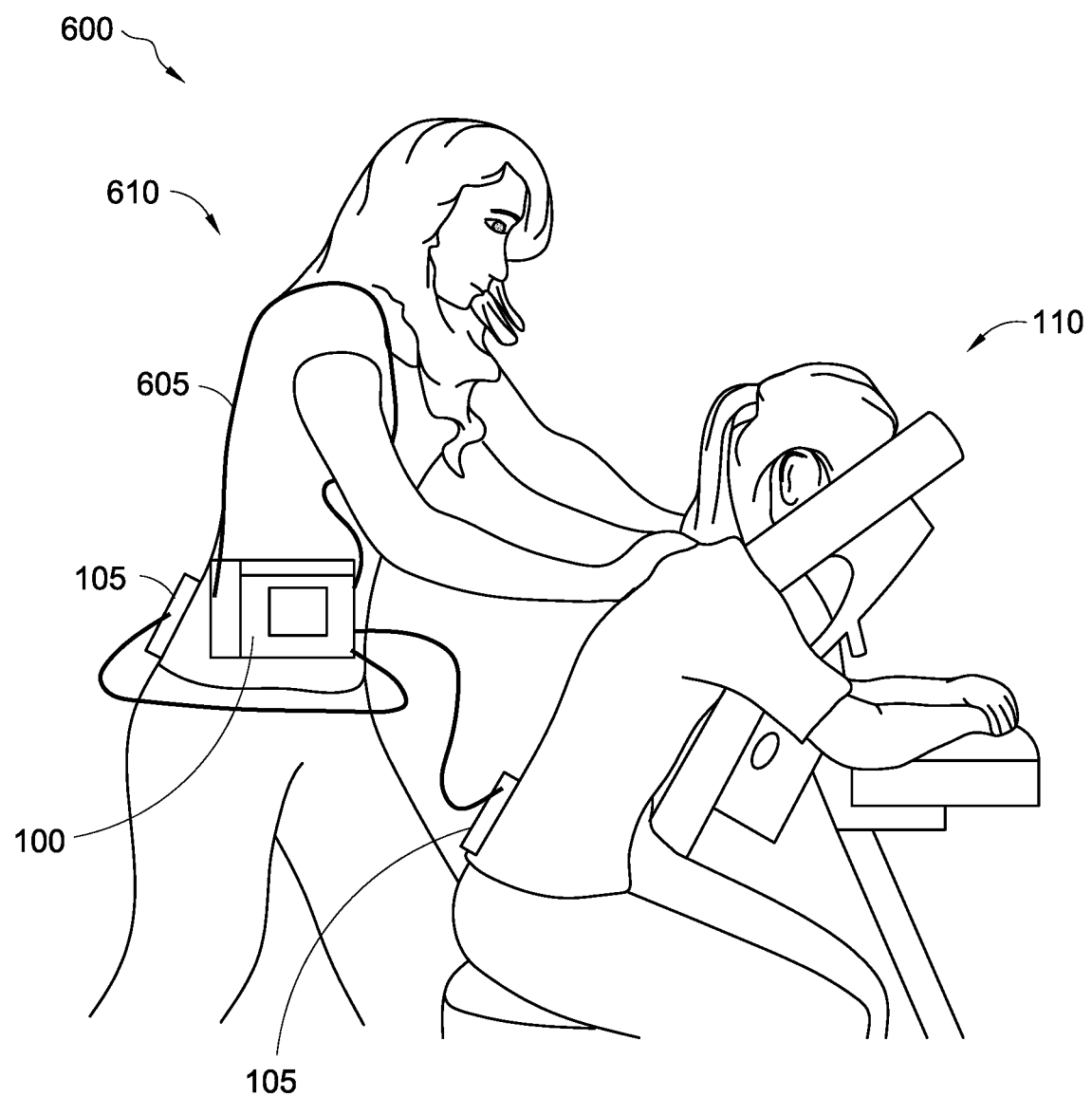
FIG. 6 is an example use-mode of the portable electrical stimulation device in accordance with aspects of this disclosure.

FIG. 6 is an example use-mode 600 of the portable electrical stimulation device 100 in accordance with aspects of this disclosure. In the use mode 600 illustrated in FIG. 6, a first one of the electrodes 105 may be placed on a first user 110 (e.g., a patient) while a second one of the electrodes 105 may be placed on a second user 610 (e.g., physical therapist, massage therapist, chiropractor or other healthcare provider (either professional or non-professional)). The portable electrical stimulation device 100 may be attached, held, or otherwise coupled to the second user 610 via a strap 605 or another capability (e.g., belt, Velcro, etc.) for attaching the portable electrical stimulation device 100 to the second user 610. However, in other embodiments, the portable electrical stimulation device 100 may be placed on a surface (e.g., a table, the floor, etc.) with the second electrode 105 electrically coupled to the second user 610 via the longer electrical wire 415. The second user 610 may complete an electrical loop between the first and second electrodes 105 using their hands by applying their hands directly to the skin of the first user 110. In certain embodiments, the electrical connection between the second user's 610 hands and the first user 110 can be improved by using a conductive cream 425 and/or another conductive massage oil. In the use mode of FIG. 6, the electrical stimulation provided by the portable electrical stimulation device 100 via the second user's 610 hands can be combined with the effects of physical therapy (e.g., via a massage) to combine the effects of the two therapies. In addition to the additive effects of the two therapies on the first user 110, the electrical stimulation through the second user's 610 hands can reduce the strain typically associated with performing a massage on the first user 110, thereby easing the burden of performing the massage.

Figure 7:
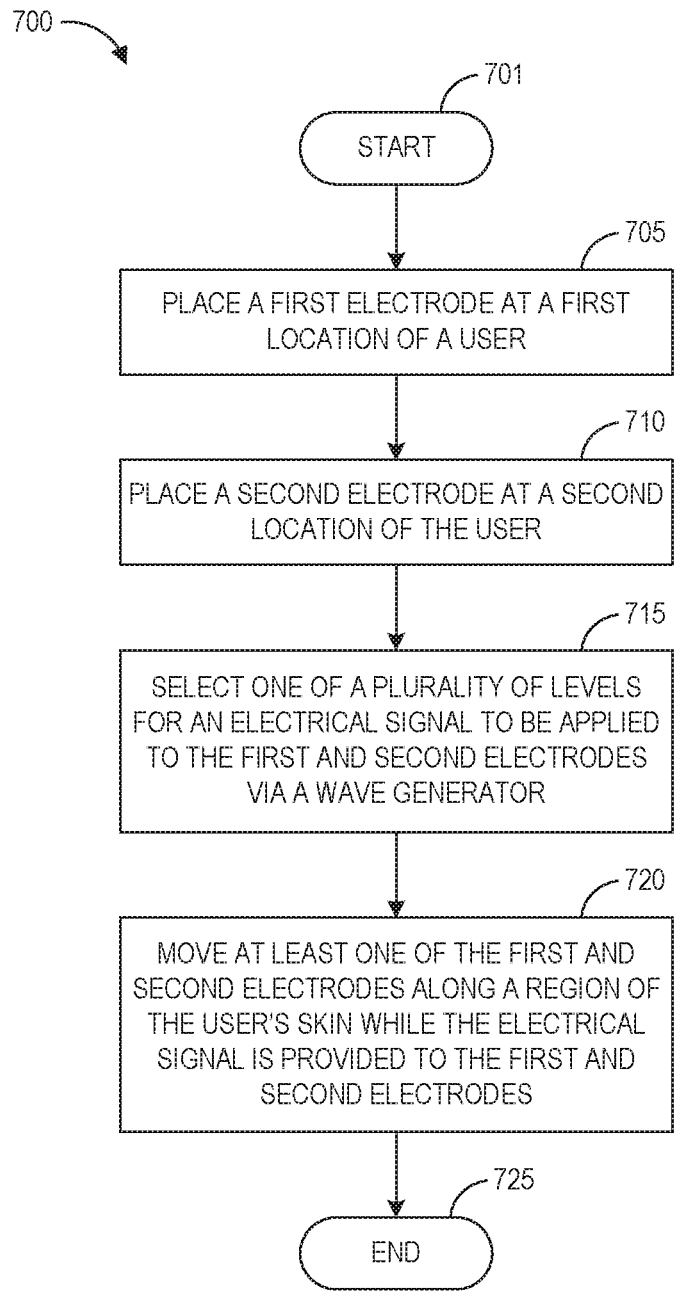
FIG. 7 is a flowchart illustrating a method of treating a user with the portable electrical stimulation device in accordance with some aspects of this disclosure.

FIG. 7 is a flowchart illustrating a method 700 of treating a user with the portable electrical stimulation device 100 in accordance with some aspects of this disclosure. The method 700 may involve a use-mode in which at least one of the electrodes is moved along a region of the user's skin. The method 700 begins at block 701. At block 705, the method 700 involves placing a first electrode 105 at a first location of a user 110. At block 710, the method 700 involves placing a second electrode 105 at a second location of the user 110. At block 715, the method 700 involves selecting one of a plurality of levels for an electrical signal to be applied to the first and second electrodes 105 via a wave generator 223. The wave generator 223 is configured to provide the electrical signal to the user 110 via the pair of electrodes 105. The levels are defined by at least a frequency, a peak voltage, and a current.

Depending on the embodiment, the user may provide input of the selected level to one or more input devices (e.g., switches 350) formed on the portable electrical stimulation device 100 and/or via voice commands received at a microphone 250 of the portable electrical stimulation device 100.

At block 720, the method 700 involves moving at least one of the first and second electrodes 105 along a region of the user's 110 skin while the electrical signal is provided to the first and second electrodes 105. In certain embodiments, the region may correspond to a region for which the user 110 desires treatment (e.g., a sore region and/or a painful region). Thus, the electrical signal may be applied to the desired region. Optionally, the method 700 may involve moving the at least one of the first and second electrodes along a sub-portion of the region in which the user 110 determines most effective in treatment of the region. The method 700 ends at block 725.

Figure 8:
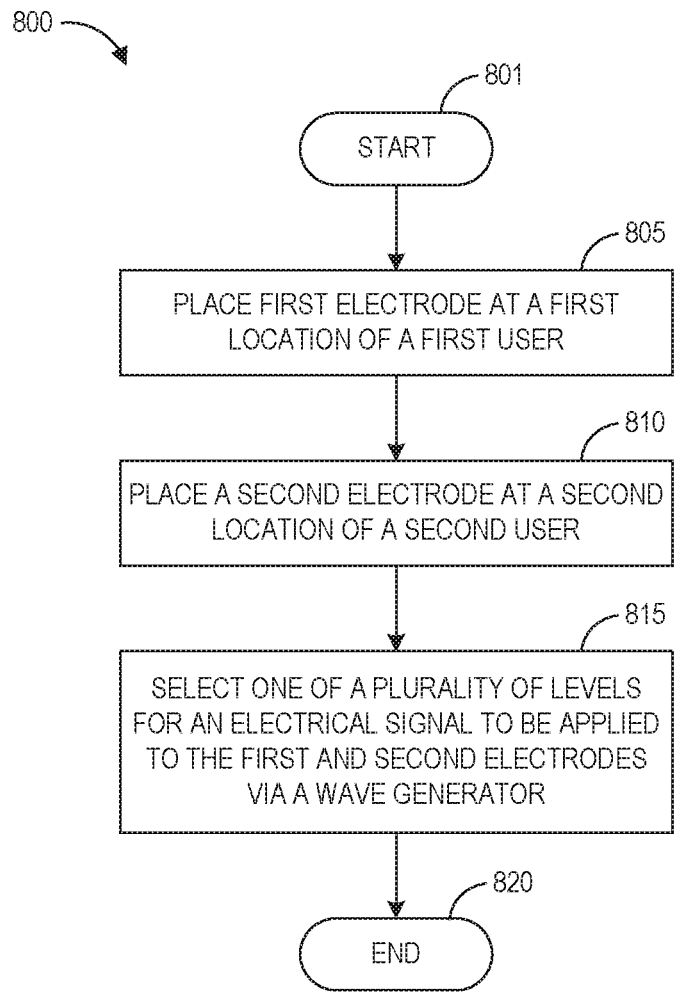
FIG. 8 is a flowchart illustrating a method of treating a user with the portable electrical stimulation device in accordance with other aspects of this disclosure.

FIG. 8 is a flowchart illustrating a method 800 of treating a user with the portable electrical stimulation device 100 in accordance with other aspects of this disclosure. The method 800 may involve a use-mode in which a second user performs a massage on a first user with assistance from the portable electrical stimulation device 100. The method 800 begins at block 801. At block 805, the method 800 involves placing a first electrode 105 at a first location of a first user 110.

At block 810, the method 800 involves placing a second electrode 105 at a second location of a second user 610. At block 815, the method 800 involves selecting one of a plurality of levels for an electrical signal to be applied to the first and second electrodes 105 via a wave generator 223.

The wave generator is configured to provide the electrical signal to the first user 110 via the pair of electrodes 105 and the second user 610. The levels are defined by at least a frequency, a peak voltage, and/or a current. The wave generator 223 is further configured to apply the electrical signal to the first and second electrodes 105 while the second user 610 is performing a massage on the first user 110, thereby forming an electrical path between the first and second electrodes 105 via direct contact between the first and second users 110 and 610. The method 800 ends at block 820.

One or more of the above-described aspects of this disclosure may result in certain advantages over other typical TENS devices. For example, the portable electrical stimulation device 100 may provide therapy for musculoskeletal challenges involving pain, inflammation, stiffness and other related body ailments via the delivery of microcurrent waves resonating with those at healthy levels of the body. The portable electrical stimulation device 100 may mimic the principles of acupuncture and western/eastern medicine and replicates many of the benefits of a deep tissue massage without discomfort. For example, the described technology can provide improvements in body health. Such improvements can include, but are not limited to, one or more of: i) reducing or eliminating pain, ii) reducing swelling, iii) stimulating and relaxing muscles and stimulating muscle tone, iv) increasing elasticity of tendons and ligaments, v) increasing patients range of motion and mobility, vi) improving circulation and blood flow throughout body and vii) assisting after training recovery and promoting the removal of toxins or lactic acids.

The described technology can also provide healing and recovery benefits. Such benefits can include, but are not limited to, one or more of: i) aiding in the treatment of various injury types, sports and everyday living, ii) promoting tissue healing and connective tissue repair and rebuilding, iii) reducing tension in muscles, tendons and relaxing body for better sleep and iv) assisting in pre and post surgery by strengthening muscle, increasing blood flow, and removal of inflammation.

The described technology can also provide improvements in preventative benefits. Such benefits can include, but are not limited to, one or more of: i) pre-warming up to loosen muscles and tendons, thereby helping prevent injury, ii) increasing flexibility and strength during warm-up and boosting body's natural energy, iii) loosening muscles and tendons and increasing blood and energy flow throughout the body, iv) reducing inflammation across body mass improving flexibility and performance and v) enhancing physiologic change at cellular level creating balance at all levels of the body.

Other Variations

The foregoing description details certain embodiments of the systems, devices, and methods disclosed herein. It will be appreciated, however, that no matter how detailed the foregoing appears in text, the systems, devices, and methods can be practiced in many ways. The use of particular terminology when describing certain features or aspects of the disclosure should not be taken to imply that the terminology is being redefined herein to be restricted to including any specific characteristics of the features or aspects of the technology with which that terminology is associated.

It will be appreciated by those skilled in the art that various modifications and changes can be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures can be combined, interchanged, or excluded from other embodiments.

With respect to the use of substantially any plural and/or singular terms herein, those having skill in the art can translate from the plural to the singular and/or from the singular to the plural as is appropriate to the context and/or application. The various singular/plural permutations can be expressly set forth herein for sake of clarity.

Directional terms used herein (for example, top, bottom, side, up, down, inward, outward, etc.) are generally used with reference to the orientation or perspective shown in the figures and are not intended to be limiting. For example, positioning "above" described herein can refer to positioning below or on one of sides. Thus, features described as being "above" may be included below, on one of sides, or the like.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations).

The term "comprising" as used herein is synonymous with "including," "containing," or "characterized by," and is inclusive or open-ended and does not exclude additional, unrecited elements or method steps.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Language of degree used herein, such as the terms "approximately," "about," "generally," and "substantially" as used herein represent a value, amount, or characteristic close to the stated value, amount, or characteristic that still performs a desired function and/or achieves a desired result. For example, the terms "approximately", "about", "generally," and "substantially" may refer to an amount that is within less than 10% of, within less than 5% of, within less than 1% of, within less than 0.1% of, and/or within less than 0.01% of the stated amount.

It will be further understood by those within the art that any disjunctive word and/or phrase presenting two or more alternative terms, whether in the description, claims, or drawings, can be understood to contemplate the possibilities of including one of the terms, either of the terms, or both terms. For example, the phrase "A or B" will be understood to include the possibilities of "A" or "B" or "A and B." Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. The described functionality may be implemented in varying ways for each particular application, but such implementation decisions should not be interpreted as causing a departure from the scope of the embodiments of the invention.

The various illustrative blocks, modules, and circuits described in connection with the embodiments disclosed herein may be implemented or performed with a general purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm and functions described in connection with the embodiments disclosed herein may be embodied directly in hardware, in a software module executed by a processor, or in a combination of the two. If implemented in software, the functions may be stored on or transmitted over as one or more instructions or code on a tangible, non-transitory computer-readable medium. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD ROM, or any other form of storage medium known in the art. A storage medium is coupled to the processor such that the processor can read information from, and write information to, the storage medium. In the alternative, the storage medium may be integral to the processor. Disk and disc, as used herein, includes compact disc (CD), laser disc, optical disc, digital versatile disc (DVD), floppy disk and blu ray disc where disks usually reproduce data magnetically, while discs reproduce data optically with lasers. Combinations of the above should also be included within the scope of computer readable media. The processor and the storage medium may reside in an ASIC. The ASIC may reside in a user terminal. In the alternative, the processor and the storage medium may reside as discrete components in a user terminal.

The above description discloses embodiments of systems, apparatuses, devices, methods, and materials of the present disclosure. This disclosure is susceptible to modifications in the components, parts, elements, steps, and materials, as well as alterations in the fabrication methods and equipment. Such modifications will become apparent to those skilled in the art from a consideration of this disclosure or practice of the disclosure. Consequently, it is not intended that the disclosure be limited to the specific embodiments disclosed herein, but that it cover all modifications and alternatives coming within the scope and spirit of the subject matter embodied in the following claims.

What is claimed is:

1. A portable electrical stimulation device, comprising:
   a wave generator configured to provide an electrical signal, the wave generator comprising a current limiter; and
   a pair of electrodes configured to be disposed on a user and to output a stimulation pulse based on the electrical signal, the current limiter disposed outside the pair of electrodes;
   one or more sensors configured to sense biometric parameters of the user;
   a biometric user identification module configured to identify the user based on the sensed biometric parameters of the user,
   wherein the wave generator is further configured to generate the electrical signal at one of a plurality of intensity levels, each of the plurality of intensity levels defined by a combination of 1) a frequency in a range of about 50 Hz-about 500 Hz, 2) a peak voltage in a range of about 40 V-about 250 V, and 3) a peak current in a range of about 25 mA-about 150 mA,
   wherein the wave generator is further configured to: generate waves having a substantially equal positive pulse width, and adjust the frequency of each of the intensity levels by altering a neutral pulse width of the waves while maintaining the positive pulse width,
   wherein the frequency and the peak voltage have a generally inverse relationship in which the peak voltage generally increases as the frequency decreases and the peak voltage generally decreases as the frequency increases, and
   wherein the wave generator further comprises:
      a microcontroller configured to generate a boost clock signal and a pulse out signal,
      a boost converter configured to receive the boost clock signal and generate a boosted signal, and
      at least one transistor configured to generate the electrical based on the pulse out signal and the boosted signal.

2. The portable electrical stimulation device of claim 1, wherein at least one of the electrodes comprises one or more sensors configured to sense the user's impedance in response to the stimulation pulse having a first intensity level being applied to the user, and wherein the wave generator is configured to automatically adjust a level of the electrical signal to a second intensity level different from the first intensity level based on the sensed user's impedance.

3. The portable electrical stimulation device of claim 2, wherein the wave generator is configured to automatically adjust the level of the electrical signal to the second intensity level greater than the first intensity level in response to the one or more sensors sensing no reaction by the user with the stimulation pulse having the first intensity level for a predetermined period of time.

4. The portable electrical stimulation device of claim 1, further comprising a memory configured to store information regarding the user and the user's reaction to intensity levels.

5. The portable electrical stimulation device of claim 1, wherein at least one of the electrodes comprises one or more sensors configured to sense the user's reaction in response to the stimulation pulse having a first intensity level being applied to the user, and wherein the wave generator is configured to automatically adjust a level of the electrical signal to a second intensity level different from the first intensity level based on the sensed user's reaction.

6. The portable electrical stimulation device of claim 5, wherein the wave generator is configured to automatically adjust the level of the electrical signal to the second intensity level less than the first intensity level in response to the sensed user's reaction indicating that the user is feeling discomfort with the stimulation pulse having the first intensity level.

7. The portable electrical stimulation device of claim 1, wherein the wave generator is further configured to generate waves that have a strictly positive voltage.

8. The portable electrical stimulation device of claim 1, wherein the wave generator is further configured to:
   receive a command to transition from a first intensity level to a second intensity level that is different from the first intensity level,
   gradually increase the peak voltage of waves to the peak voltage associated with the second intensity level in response to the received command.

9. The portable electrical stimulation device of claim 1, wherein the wave generator comprises an output terminal, and wherein the current limiter is arranged in series with the output terminal of the wave generator.

10. The portable electrical stimulation device of claim 1, wherein the current limiter comprises a resistive element.

11. The portable electrical stimulation device of claim 1, wherein the wave generator is wiredly or wirelessly connected to the electrodes.

12. The portable electrical stimulation device of claim 3, wherein the wave generator is configured to generate the electrical signal based on the information stored on the memory.

13. The portable electrical stimulation device of claim 1, wherein each of the electrodes comprises:
   a filter;
   a high density sponge placed over the filter;
   a flexible conductive contact placed over the high density sponge;
   a cover covering the flexible conductive contact; and
   an electrical wire connected to the flexible conductive contact.

14. The portable electrical stimulation device of claim 1, wherein at least one of the electrodes has one of the following shapes: a circular shape, a square shape or other polygonal shape.

15. The portable electrical stimulation device of claim 1, wherein each of the intensity levels is predefined.

16. The portable electrical stimulation device of claim 1, wherein the wave generator is further configured to generate the peak voltage so as to increase from about 56V to about 156V in response to the frequency decreasing from about 328 Hz to about 60 Hz, when there is a body load.

17. The portable electrical stimulation device of claim 1, wherein the wave generator is further configured to generate the peak voltage is configured to increase from about 92V to about 210V in response to the frequency decreasing from about 328 Hz to about 60 Hz, when there is no load.

18. The portable electrical stimulation device of claim 1, wherein the wave generator is further configured to generate waves that have a strictly positive current.

19. The portable electrical stimulation device of claim 1, wherein the peak voltage generally increases as the plurality of intensity levels increase from a first level to a second level higher than the first level and the frequency generally decreases as the plurality of intensity levels increase from the first level to the second level.

20. The portable electrical stimulation device of claim 1, wherein the frequency is in the range of 50 Hz to about 500 Hz, and the voltage is in the range of 60 V to about 250 V.

21. The portable electrical stimulation device of claim 1, wherein the current limiter comprises a negative temperature coefficient (NTC) thermistor.

* * * * *